United States Patent
Whitehead et al.

(10) Patent No.: US 8,541,243 B2
(45) Date of Patent: Sep. 24, 2013

(54) METHOD FOR ASSESSMENT OF FOLATE PHENOTYPES, DISEASE RISK AND RESPONSE TO THERAPY

(75) Inventors: Alexander Steven Whitehead, Wayne, PA (US); Ian A. Blair, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 148 days.

(21) Appl. No.: 13/002,758

(22) PCT Filed: Jul. 8, 2009

(86) PCT No.: PCT/US2009/049967
§ 371 (c)(1),
(2), (4) Date: May 10, 2011

(87) PCT Pub. No.: WO2010/006070
PCT Pub. Date: Jan. 14, 2010

(65) Prior Publication Data
US 2011/0207164 A1 Aug. 25, 2011

Related U.S. Application Data

(60) Provisional application No. 61/134,364, filed on Jul. 8, 2008.

(51) Int. Cl.
*G01N 33/82* (2006.01)
*G01N 33/42* (2006.01)
*G01N 33/00* (2006.01)
*G01N 30/02* (2006.01)

(52) U.S. Cl.
USPC ............ 436/501; 435/29; 73/61.52; 73/61.43

(58) Field of Classification Search
USPC ............ 436/98, 96, 91; 435/29, 4; 73/61.43, 73/61.41
See application file for complete search history.

(56) References Cited

U.S. PATENT DOCUMENTS
2006/0286571 A1  12/2006  Dervieux

OTHER PUBLICATIONS

Barber et al., "Investigation of folate pathway gene polymorphisms and the incidence of neural tube defects in a Texas hispanic population." 2000, Mol Genet Metab 70(1):45-52.

Beaudin et al., "Folate-mediated one-carbon metabolism and neural tube defects: balancing genome synthesis and gene expression." 2007, Birth Defects Res C Embryo Today 81(3):183-203.

Blount et al., "Folate deficiency causes uracil misincorporation into human DNA and chromosome breakage: implications for cancer and neuronal damage." 1997, Proc. Natl. Acad. Sci. USA 94(7):3290-5.

Brown et al., "Mild folate deficiency induces a proatherosclerotic phenotype in endothelial cells." 2006, Atherosclerosis 189:133-41.

Fazili et al., "Measurement of folates in serum and conventionally prepared whole blood lysates: application of an automated 96-well plate isotope-dilution tandem mass spectrometry method." 2004, Clin. Chem. 50(12):2378-81.

Golbahar et al., "Association of red blood cell 5-methyletrahydrofolate with bone mineral density in postmenopausal Iranian women." 2005, Osteoporos Int 16:1894-1998.

Golbahar et al., "Distribution of 5, 10-methylenetetrahydrofolate reductase (C667T) polymorphism and its association with red blood cell 5-methyltetrahydrofolate in healthy Iranians." 2005, Clinical Nutrition 24:83-87.

Horne, "Neither methionine nor nitrous oxide inaction of methionine synthase affect the concentration of 5, 10-methylenetetrahydrofolate in rat liver." 2003, J Nutr 133:476-478.

Huang et al., "Quantification of intracellular homocysteine by stable isotope dilution liquid chromatography/tandem mass spectrometry." 2007 Biomed Chromatogr 21:107-12.

Lucock, "Synergy of genes and nutrients: the case of homocysteine." 2006 Curr Opin Clin Nutr Metab Care; 9:748-56.

Mitchell et al., "Spina bifida." 2004 Lancet 364:1885-95.

Shields et al., "The "thermolabile" variant of methylenetetrahydrofolate reductase and neural tube defects: An evaluation of genetic risk and the relative importance of the genotypes of the embryo and the mother." 1999, Am J Hum Genet 64(4):1045-1055.

Zhu et al., "Determination of cellular redox status by stable isotope dilution liquid chromatography/mass spectrometry analysis of glutathione and glutathione disulfide." 2008, Rapid Commun. Mass Spectrom. 22(4):432-40.

*Primary Examiner* — Christine T Mui
(74) *Attorney, Agent, or Firm* — Riverside Law LLP

(57) ABSTRACT

The invention provides a method for measuring the levels of 5-methyltetrahydrofolate (5-MTHF), tetrahydrofolate (THF), and 5,10-MTHF in a biological sample. The method includes employing an isotope dilution liquid chromatography-multiple reaction monitoring/mass spectrometry (LC-MRM/MS) methodology.

16 Claims, 7 Drawing Sheets

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial
<220> FEATURE:
<223> OTHER INFORMATION: Chemically synthesized primer

<400> SEQUENCE: 1
gcagggagct ttgaggctga cc                                          22

<210> SEQ ID NO 2
<211> LENGTH: 21
<212> TYPE: DNA
<213> ORGANISM: Artificial
<220> FEATURE:
<223> OTHER INFORMATION: Chemically sythesized primer

<400> SEQUENCE: 2
tggggcaagt gatgcccatg t                                           21

<210> SEQ ID NO 3
<211> LENGTH: 17
<212> TYPE: DNA
<213> ORGANISM: Artificial
<220> FEATURE:
<223> OTHER INFORMATION: Chemically synthesized probe

<400> SEQUENCE: 3
atgaaatcga ctcccgc                                                17

<210> SEQ ID NO 4
<211> LENGTH: 17
<212> TYPE: DNA
<213> ORGANISM: Artificial
<220> FEATURE:
<223> OTHER INFORMATION: Chemically synthesized probe
```

-continued

```
<400> SEQUENCE: 4
atgaaatcgg ctcccgc                                                      17

<210> SEQ ID NO 5
<211> LENGTH: 19
<212> TYPE: DNA
<213> ORGANISM: Artificial
<220> FEATURE:
<223> OTHER INFORMATION: Chemically synthesized primer

<400> SEQUENCE: 5
gaggagctgc tgaagatgt                                                    19

<210> SEQ ID NO 6
<211> LENGTH: 20
<212> TYPE: DNA
<213> ORGANISM: Artificial
<220> FEATURE:
<223> OTHER INFORMATION: Chemically synthesized primer

<400> SEQUENCE: 6
cgagaggtaa agaacgaaga                                                   20

<210> SEQ ID NO 7
<211> LENGTH: 16
<212> TYPE: DNA
<213> ORGANISM: Artificial
<220> FEATURE:
<223> OTHER INFORMATION: Chemically synthesized probe

<400> SEQUENCE: 7
agacacttgc ttcact                                                       16

<210> SEQ ID NO 8
<211> LENGTH: 16
<212> TYPE: DNA
<213> ORGANISM: Artificial
<220> FEATURE:
<223> OTHER INFORMATION: Chemically synthesized probe

<400> SEQUENCE: 8
caaagacact ttcttc                                                       16
```

METHOD FOR ASSESSMENT OF FOLATE PHENOTYPES, DISEASE RISK AND RESPONSE TO THERAPY

CROSS-REFERENCE TO RELATED APPLICATIONS

The present application is a U.S. national phase application filed under 35 U.S.C. §371 claiming benefit to International Patent Application No. PCT/US2009/49967, filed on Jul. 8, 2009, which is entitled to priority under 35 U.S.C. §119(e) to U.S. Provisional Patent Application No. 61/134,364, filed on Jul. 8, 2008, which applications are incorporated by reference herein in their entireties.

STATEMENT REGARDING FEDERALLY SUPPORTED RESEARCH OR DEVELOPMENT

This invention was supported, in part, by National Institutes of Health grant numbers RO1AR47663, RO1CA108862, and P30ES0135080. The government has certain rights in the invention.

BACKGROUND OF THE INVENTION

Folate is a B vitamin acquired by dietary consumption of leafy green vegetables, whole grains and other food sources. Folic acid is the synthetic form of folate that may be taken in supplement form or as an additive to milled grain products and other manufactured/processed foods.

Folate is a B vitamin that is centrally involved in one carbon metabolism. It is important for facilitating cellular methylation reactions involving substrates such as DNA, proteins and lipids, as well as xenobiotics and prescription medications, and for generating thymidylate and purines (Stover, 2004, Nutr Rev 62:S3-12). RBC folate concentrations are generally measured as "total folate" without distinguishing between the several forms of folate that are present. This potentially limits the predictive value of such measurements. The major circulating form of folate is 5-methyltetrahydrofolate (5-$CH_3$-THF or 5-MTHF). Intracellular 5-$CH_3$-THF, derived from 5,10-methylenetetrahydrofolate, is used to remethylate homocysteine (Hcy) to methionine, which in turn is converted to the universal methyl donor S-adenosyl methionine. In the latter reaction, 5-$CH_3$-THF is converted to tetrahydrofolate (THF). Alternatively, to facilitate nucleic acid synthesis, 5,10-methylenetetrahydrofolate is converted via 5,10-methenyltetrahydrofolate (5,10-methenylTHF) and formylated derivatives to THF. Thus, 5-$CH_3$-THF, THF and 5,10-methenylTHF represent distinct folate derivatives that play key roles within the methylation and nucleic acid synthesis compartments of folate/Hcy metabolism.

Folate/Hcy metabolism provides one-carbon units for many essential biological processes (Selhub, 2002, J Nutr Health Aging 6(1):39-42; Stover, 2004, Nutr Rev 62:83-12; Smulders et al., 2005, Semin, Vasc. Med, 5(2):87-97; Huang et al., 2007, Biomed, Chromatogr. 21:107-12). In particular, it enables the methylation of substrates including DNA, proteins and lipids, and the generation of thymidylate and purines, important functions that require different intracellular folate derivatives (Brown et al., 2006, Atherosclerosis 189:133-41). Low folate status is associated with elevated levels of circulating homocysteine (hyperhomocysteinemia), (Huang et al., 2007, Biomed. Chromatogr. 21:107-12) and a phenotype characterized by low red blood cell (RBC) and serum folate together with high homocysteine has been implicated in many diverse human pathologies ranging from neural tube defects such as spina bifida (Pitkin, 2007, Am. J. Clin. Nutr. 85:285S-288S; Jensen et al., 2006, Am. J. Med. Genet. A 140:1114-8) to aging-related conditions such as cardiovascular disease (Smulders et al., 2005, Semin. Vasc. Med. 5(2): 87-97) and colorectal cancer (Kim, 2007, Mol. Nutr. Food Res 51(3):267-92; Sanderson et al., 2007, Br. J. Nutr. 98(6): 1299-304). In addition, individuals with a low folate/high homocysteine phenotype are at elevated risk of many pathologies including, but not restricted to, coronary artery disease, cerebrovascular disease, peripheral vascular disease, thrombosis, inflammatory bowel disease, Alzheimer's disease, some cancers, and some neuropsychiatric diseases. In pregnancy, the phenotype has been associated with spina bifida, Down syndrome, early spontaneous abortion, premature birth and pre-eclampsia. In the elderly, the phenotype is associated with cognitive decline. Folate dysregulation negatively impacts several key cellular functions.

In addition, the potentially deleterious effects of hyperhomocysteinemia are a consequence of inadequate levels of the methyl donor 5-methyltetrahydrofolate (5-MTHF) (Brown et al., 2006, Atherosclerosis 189:133-41; Blount et al., 1997, Proc. Natl. Acad. Sci. USA 94(7):3290-5). Folate/homocysteine metabolism also modulates glutathione biosynthesis through the cystathionine/cysteine pathway, which is in turn crucial for controlling intracellular redox status (Zhu et al., 2008, Rapid Commun. Mass Spectrom. 22(4):432-40).

Mild hyperhomocysteinemia, characterized by high (>13 µmol/L) circulating concentrations (Jacques et al., 1999 N Engl J Med 340:1449-54) of the intermediate amino acid homocysteine, has been associated with a wide range of human pathologies including cardiovascular disease (Refsum et al., 1998 Ann Rev Medicine 49:31-62), stroke (Furie et al., 2006 Semin Neurol 26:24-32), Alzheimer disease (Seshadri et al., 2006 J Alzheimers Disease 9:393-8), cognitive impairment (Durga et al., 2007 Lancet 369:208-16), inflammatory bowel disease (Mahmud et al., 1999 Gut 45:389-94), some cancers (Powers et al., 2005 J Nutr 2005 135:2960S-66S), and adverse reproductive outcomes, including birth defects such as spina bifida (Mitchell et al., 2004 Lancet 364:1885-95). In a clinical setting, measurements of plasma total Hcy (tHcy) are conducted for a variety of purposes such as cardiovascular disease risk assessment and the management of patients taking anti-folate drugs. As elevated mild hyperhomocysteinemia is often underpinned by sub-optimal folate status (Jacques et al., 1996 Circulation 93:7-9; Harmon et al.,1996 Q J Med 1996 89:571-7), concurrent measurements of plasma folate and red blood cell (RBC) folate are often conducted.

There is a well-established reciprocal relationship between folate and tHcy (Jacques et al., 1996 Circulation 93:7-9; Harmon et al., 1996 Q J Med 89:571-7). In addition to hyperhomocysteinemia, low folate status can lead to impaired methylating capacity, compromised nucleic acid synthesis, and increased glutathione production, all of which have pathogenic potential (Stover et al., 2004 Nutr Res 62: 3-12). The importance of adequate folate status for preventing spina bifida is well established (Czeizel, 1992 N Engl J Med 327: 1832-5; Barry et al., 1999 N Engl J Med 341:1485-90). Indeed, to reduce the prevalence of birth defects such as spina bifida, folic acid fortification of milled grain products was mandated in the United States in 1998.

Over the past two decades, many clinical studies have sought to characterize folate/Hcy metabolism in order to identify biochemical features that are associated with particular pathologies. In addition, studies of folate/Hcy phenotypes in healthy populations have been undertaken to examine the determinants of plasma and RBC folate levels and to assess the need for, or consequence of, folic acid supplementation and fortification. Many of these studies have relied on biochemical measurements that have been made in clinical laboratories using standard analytical methods and, for RBC folate, have considered only total folate levels.

Over the past ten years several functional polymorphisms in enzymes involved in folate/homocysteine metabolism have been described (Schwahn et al., 2001, Am. J. Pharmacogenomics 1(3):189-201). The functional polymorphism with the most readily observed impact on phenotype is the C to T transition at nucleotide 677 (677C>T) of the methylenetetrahydrofolate reductase (MTHFR) gene, which results in a change in amino acid residue from Ala>Val at position 222, located at the bottom of the ($\beta\alpha$)8 barrel of the catalytic domain of the enzyme (Pejchal et al., 2006, Biochemistry 45(15):4808-18). The 677T allele encodes an enzyme that is 'thermolabile' and less efficient at generating the 5-MTHF that is needed for both homocysteine remethylation and the generation of S-adenosyl methionine for methylation reactions. It is well established that MTHFR 677TT homozygotes with low folate status are at greatly increased risk of being hyperhomocysteinemic (Strain et al., 2004, Proc. Nutr. Soc. 63(4):597-603). Selhub and colleagues have established that in the RBCs of individuals with this genotype, 5-MTHF comprises only 60% of total RBC folate, whereas this form predominates in the RBCs of their 677CC peers (Bagley et al., 1998, Proc. Natl. Acad. Sci USA 95(22):13217-20; Davis et at, 2005, J. Nutr. 135(5):1040-4). Subsequently, it has been shown that the MTHFR C677T genotype is the primary determinant of non-methylfolate accumulation in RBCs (Botta et at, 2000, Am. J. Epidemiol. 151(9):862-77). The homozygous MTHFR 677TT genotype confers a significantly increased risk of many of the conditions with which a low folate, high homocysteine phenotype has been associated, for example, approximately 2-fold for spina bifida (Lewis et at, 2005, BMJ. 331(7524):1053), and 1.15-fold for cardiovascular disease (Smulders et al., 2007, J. Nutt Biochem. 18(10): 693-9). However, the excess individual risk of developing such conditions in relation to their prevalence is insufficient to warrant genetic testing and counseling. Therefore, there is a need to establish laboratory methods to define the degree of variation in the 'folate phenotypes' between and within the three MTHFR 677C>T genotypes in order to determine whether there are subsets of TT homozygotes, and possibly of CT heterozygotes, with extreme phenotypes that may be associated with greatly enhanced risk. Individuals falling into such subsets might benefit from early identification and intervention.

Several drugs have been designed to disrupt specific aspects of folate/homocysteine metabolism in order to produce therapeutic effects in the context of a wide range of disease including auto-immune/inflammatory disease and cancer. For example methotrexate (MTX) is widely used in rheumatoid arthritis (as well as leukemia) and 5-fluorouracil (5-FU) is the mainstay of many solid tumor treatment protocols.

Clinical laboratory tests are available to measure serum/plasma folate and Red Blood Cell (RBC) folate. The latter is currently the preferred mean for assessing recent folate history as RBCs retain the folates that are present at erythropoiesis through their 120-day life cycle. Such tests are used, sometimes in conjunction with Hcy measurements, to determine whether folic acid supplements should be prescribed/recommended to: correct deficiency/insufficiency; reduce the risk of cardiovascular disease, birth defects and other pathologies; mitigate the side effects of drugs with anti-folate properties, including MTX and 5-FU.

Cellular folate, including RBC folate, is not a single chemical entity. There are several forms of folate and each participates in different metabolic processes, including methylation and nucleic acid synthesis. The ability to measure "folate" using standard tests therefore provides only quantitative information and lacks the qualitative resolution to provide information regarding the support of diverse cellular functions, the disruption of which might be pathogenic, and require remediation.

In humans, defects of neurulation are relatively common and result in serious malformations, including anencephaly and spina bifida (Mitchell et al., 2004, Lancet 364(9448): 1885-1895). Collectively, these malformations are referred to as neural tube defects (NTDs). While a small proportion of fetuses/infants affected by an NTD are identified as having an underlying syndrome, no specific cause(s) can be identified in the majority. However, a portion of NTDs in this latter group can be prevented by maternal periconceptional supplementation with folic acid (1991 Lancet 338(8760):131-137; Czeizel et al., 1992, N Engl J Med 327(26):1832-1835). In the absence of such supplementation, pregnancies that result in NTD birth outcome are characterized by low maternal folate status (Kirke et al., 1993, Q J Med 86(11):703-708; Mills et al., 1995, Lancet 345(8943):149-151). This suggests that folic acid is corrective rather than pharmacologically active, and therefore that there may be a causative relationship between maternal folate insufficiency (or dysregulation) and failure of neurulation very early in development. However, the precise mechanism(s) by which low folate status contributes to NTD etiology remains unknown.

The protective effect of maternal periconceptional folic acid has generated considerable interest in the identification of genetic variants that are associated with the risk of NTDs due to their impact on folate transport, metabolism or excretion (Beaudin et al., 2007, Birth Defects Res C Embryo Today 81(3):183-203). However, only one such variant, the 5,10-methylenetetrahydrofolate reductase (MTHFR) 677C>T single nucleotide polymorphism (SNP), has been strongly (although not unequivocally) implicated as an NTD risk factor (Barber et al., 2000, Mol Genet Metab 70(1):45-52; Shields et al., 1999, Am J Hum Genet 64(4):1045-1055). Consequently, there is interest in expanding the list of genetic candidates for NTDs to include genes that are biologically linked to other known or suspected NTD risk factors, including maternal obesity, diabetes, and hyperthermia (e.g. fever).

Many of the known NTD risk factors (e.g. diabetes, obesity) have inflammatory features, suggesting that genes involved in the inflammatory response may be involved in the etiology of this group of conditions. Interestingly, it has been shown, in a cultured endothelial cell line, that folate insufficiency induces increased synthesis and export of monocyte chemoattractant protein 1 (MCP-1), a potent pro-inflammatory chemokine (Brown et al., 2006, Atherosclerosis 189(1): 133-141). In turn, MCP-1 acts in an autocrine fashion to elicit changes in cell morphology, including the acquisition of actin stress fibers (Brown et al., 2006, Atherosclerosis 189(1):133-141). Since actin dynamics underpin cellular shape changes such as those required for convergent extension during neurulation (Schoenwolf et al., 1990, Development 109(2):243-270), alterations of MCP-1 levels could have a direct effect on morphogenesis. Furthermore, MCP-1, together with other chemokines and cytokines, appears to be important in signaling between the embryo and endometrium during implantation and placentation (Kayisli et al., 2002, Am J Reprod Immunol 47(4):213-221), which occurs just prior to neurulation. Hence, altered MCP-1 expression could also influence the risk of NTDs through modulation of maternal inflammatory responses.

The (-2518) A>G promoter polymorphism of CCL-2, the gene encoding MCP-1, confers differential responsiveness to Interleukin-1 (IL-1) (Rovin et al., 1999, Biochem Biophys Res Commun 259(2):344-348)and is, therefore, a logical NTD genetic candidate that is only indirectly related to folate metabolism. Evaluation of this polymorphism in a large number of spina bifida ease-parent triads indicated that maternal CCL-2 genotype is associated with the risk of spina bifida in offspring (Jensen et al., 2006, Am J Med Genet A 140(10): 1114-1118). Specifically, women with the CCL-2 (-2518) AA genotype appear to be at higher risk of having offspring affected with spina bifida than women with the AG or GG genotypes. As monocytes from CCL-2 AA homozygotes are known to produce less MCP-1 (as compared to those from CCL-2 AG heterozygotes or GG homozygotes) in response to IL-1, the observed increased risk of spina bifida in the offspring of women with the CCL-2 (-2518) AA genotype was hypothesized to be due to a sub-optimal systemic and/or local immune or inflammatory response resulting from low MCP-1 levels at the time of neural tube closure. However, as the CCL-2 (-2518)A>G polymorphism is not the only determinant of MCP-1 levels this explanation may be overly simplistic.

In addition to the CCL-2 (-2518)A>G polymorphism, variables that have been associated with MCP-1 levels include sex, age, race, diabetes, obesity, smoking status and the region of chromosome 3 that contains the chemokine receptor gene cluster, which includes the receptor for MCP-1 (Bielinski et al., 2007, Genes Immun 8(8):684-690; McDermott et al., 2005, Circulation 112(8):1113-1120). However, there are no published studies that have focused on the potential determinants of MCP-1 levels in reproductive age females.

There exists a long-felt need to develop novel methods to accurately identify and quantify the key forms of folate which are present in different parts of folate/homocystein metabolism and that have the potential to differentially diagnose and assess the risk of particular pathologies, and to predict/monitor responses to vitamin supplements (folic acid and other B vitamins) and anti-folate medications. In addition, there is a need to develop novel methods to accurately identify genetic and environmental variables that influence MCP-1 levels in women at risk of having an NTD affected pregnancy. The present invention meets these needs.

BRIEF SUMMARY OF THE INVENTION

The invention provides a method of measuring the level of folate in a biological sample derived from a subject comprising measuring the level of at least one of 5-methyltetrahydrofolate (5-MTHF), tetrahydrofolate (THF), and 5,10-MTHF in the biological sample, wherein the measured level of at least one of 5-MTHF, THF, and 5,10-MTHF, is a measurement of the folate level in the biological sample.

In one embodiment, at least one of 5-methyltetrahydrofolate (5-MTHF), THF, and 5,10-MTHF is measured using a methodology selected from the group consisting of an isotope dilution liquid chromatography-multiple reaction monitoring/mass spectrometry (LC-MRM/MS), an antibody-based assay, a radiometric assay, a chromatographic assay, and a microbiological assay.

In one embodiment, the levels of at least one of 5-MTHF, THF, and 5,10-MTHF is a prediction of the level of total homocysteine (tHcy) in the biological sample.

In another embodiment, measuring at least one of 5-MTHF, THF, and 5,10-MTHF as a prediction of the level of tHcy, results in a decreased incidence of misclassification of a subject as being hyperhomocysteineic compared with a method of predicting the level of tHcy that does not take into account levels of 5-MTHF, THF, and 5,10-MTHF.

In another embodiment, the level of 5-MTHF is inversely related to the level of tHcy. In yet another embodiment, the level of THF and 5,10-methenylTHF is directly related to the level of tHcy.

In one embodiment, the levels of each 5-MTHF, THF, and 5,10-MTHF are expressed as a ratio value relative to each other such that the ratio value is predictive of a disease state or disease risk of the subject.

In one embodiment, when the levels of 5-MTHF, THF, and 5,10-MTHF are measured and are summed together, the summed level predicts the level of tHcy in the biological sample.

In one embodiment, the sample is selected from the group consisting of blood, serum, plasma, whole blood, plasma, serum, red blood cells, white blood cells, neutrophils, biopsy, spinal fluid, and cellular extracts.

The invention provides a method of identifying a subject that is at risk of having a disease or condition associated with folate/homocysteine metabolism. In one embodiment, the method comprises measuring the level of folate in a biological sample derived from the subject comprising measuring the level of at least one of 5-MTHF, THF, and 5,10-MTHF in the biological sample, wherein the measured level of at least one of 5-MTHF, THF, and 5,10-MTHF, is a measurement of the folate level in the biological sample, wherein a low level of folate in the biological sample compared to the folate level in a biological sample from an otherwise identical healthy subject identifies a subject at risk of having the disease or condition.

The invention provides a method of evaluating the effect of an agent on a subject having a disease associated with folate/homocysteine metabolism. In one embodiment, the method comprises comparing the levels of at least one of 5-MTHF, THF, and 5,10-MTHF in a biological sample of a subject following administration of the agent to the subject, to levels of at least one of 5-MTHF, THF, and 5,10-MTHF in an otherwise identical biological sample of a subject not administered the agent, wherein an increased level of at least one of 5-MTHF, THF, and 5,10-MTHF detected in the biological sample of the subject administered the agent compared to the level of at least one of 5-MTHF, THF, and 5,10-MTHF in the otherwise identical biological sample is an indication that the agent increases folate levels in the subject, further wherein a decrease level of at least one of 5-MTHF, THF, and 5,10-MTHF detected in the biological sample of the subject administered with the agent compared to the level of at least one of 5-MTHF, THF, and 5,10-MTHF in the otherwise identical biological sample of the subject not administered with the agent is an indication that the agent is able to decrease folate levels in the subject.

In one embodiment, the agent generates a side effect in the subject.

In another embodiment, the agent is selected from the group consisting of an anti-inflammatory agent, an anti-tumor agent, an anti-folate agent, a nutritional supplement, a dietary supplement, and a vitamin supplement, dietary regulator, and a chemical associated with smoking.

In yet another embodiment, the side effect is selected from the group consisting of inflammation, oxidative stress, nausea, gastrointestinal disturbance, fatigue, and malaise.

The invention provides a method of diagnosing a disease or condition associated with folate/homocysteine metabolism in a subject. In one embodiment, the method comprises measuring the level of folate in a biological sample derived from a subject comprising measuring the level of at least one of 5-MTHF, THF, and 5,10-MTHF in the biological sample, wherein the measured level of at least one of 5-MTHF, THF, and 5,10-MTHF, is a measurement of the folate in the biological sample, wherein a low level of folate in the biological sample compared to the level of folate in a biological sample from an otherwise identical healthy subject identifies a subject at risk of having the disease or condition.

The invention provides a method of monitoring the progression of a disease or condition associated with folate/homocysteine metabolism in a subject. In one embodiment, the method comprises measuring the level of folate in a biological sample derived from the subject comprising measuring the level of at least one of 5-MTHF, THF, and 5,10-MTHF in the biological sample, wherein the measured level of at least one of 5-MTHF, THF, and 5,10-MTHF, is a measurement of the folate in the biological sample, wherein a low level of folate in the biological sample compared to the level of folate in a biological sample from the subject at an earlier time identifies progression of the disease or condition.

The invention provides a method of monitoring the progression of a side effect in a subject. In one embodiment, the method comprises measuring the level of folate in a biological sample derived from the subject comprising measuring the level of at least one of 5-MTHF, THF, and 5,10-MTHF in the biological sample, wherein the measured level of at least one of 5-MTHF, THF, and 5,10-MTHF, is a measurement of the folate in the biological sample, wherein a low level of folate in the biological sample compared to the folate level in a biological sample from the subject at an earlier time identifies progression of the side effect.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A through 2D, is an image depicting a full scan (upper panel) and product of ion specta (lower panel) of folates. In the full scan mode, FA, THF, 5-MTHF, and 5,10-MTHF had precursor ions at m/z 442, 446, 460, and 456, respectively (FIGS. 2A through 2D).

DETAILED DESCRIPTION OF THE INVENTION

Figure 1:
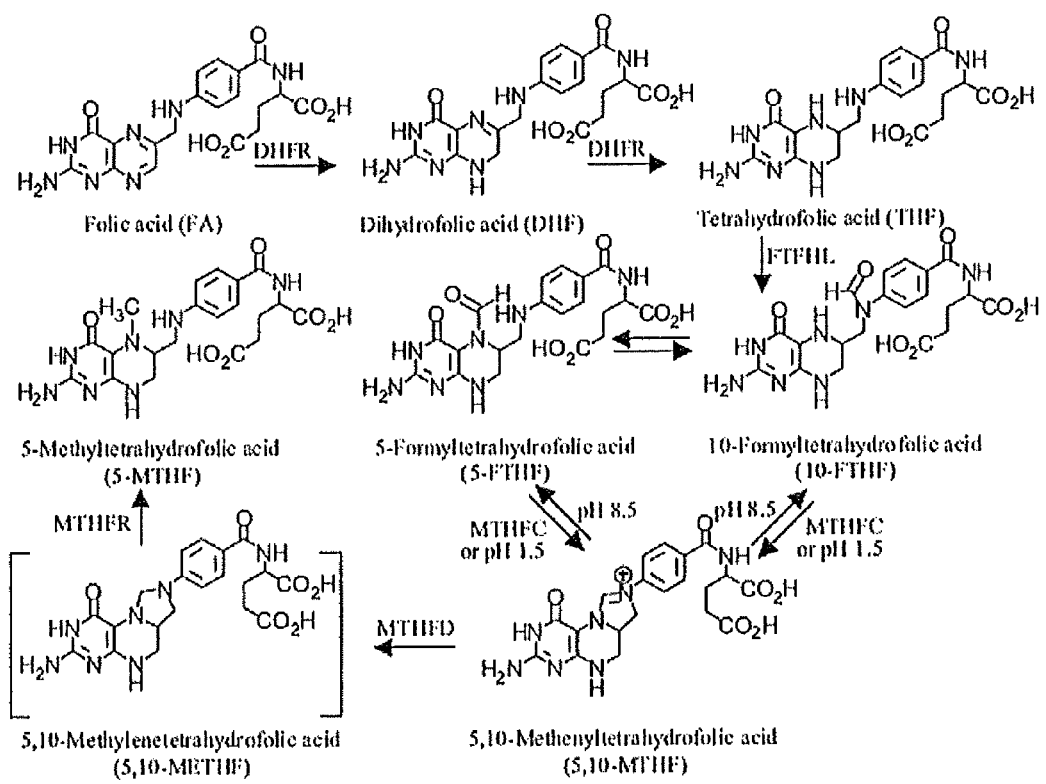
FIG. 1 is a schematic of the biosynthesis and interconversion of folates. 5-FTHF and 10-FTHF undergo dehydration to 5,10-MTHF under acidic conditions in a pH-dependent manner.

The present invention provides diagnostic methods and markers, prognostic methods and markers, and therapy evaluators for diseases or conditions associated with folate/homocysteine metabolism. In some instances, the disease or condition is associated with low folate and elevated levels of homocysteine. Such diseases include but are not limited to neural tube defects such as spina bifida; aging-related conditions such as cardiovascular disease and colorectal cancer; and high oxidative and nitrative stress such rheumatoid arthritis, vasculitis, inflammatory bowel disease, sepsis, atherosclerosis, and Alzheimer's disease. In other instance, the disease or condition is associated with elevated levels of folate.

In one aspect, a diagnostic method for identifying a subject at risk of having a disease or condition associated with low folate status and elevated levels of homocysteine is provided. In one embodiment, the method comprises assessing the amount of any combination of RBC folic acid, 5-methyltetrahydrofolate (5-MTHF), tetrahydrofolate (THF), and 5,10-MTHF in a biological sample.

RBC folate concentrations are generally measured as "total folate" without distinguishing between the several forms of folate that are present. This potentially limits the predictive value of such measurements. The present invention provides a method of detecting the levels of various forms of folate in order to determine the level of total folate. The summation of the levels of various folate together provides a more precise measurement of total folate.

In another aspect, the levels of various forms of folate are used to determine the level of total homocysteine (tHcy). The method of detecting the levels of different forms of folate as a measurement of tHcy decreases the incidence of misclassification of an individual being hyperhomocysteineic compared to a method of detecting tHcy that does not take into account the different forms of folate.

In some instances, the level of 5-MTHF is inversely related to the level of tHcy. In another embodiment, the level of THF and 5,10-methenylTHF is directly related to the level of tHcy. Thus, the present invention provides a more precise method of assessing the level of folate with respect the level of homocysteine. A utility of assessing the various forms of folate, individually and together, as absolute values and as ratios relative to each other, is the ability to predict concentrations of other biomarkers of disease state and disease risk.

Also provided are prognostic methods for monitoring the progression of a disease or condition associated with low folate status and elevated levels of homocysteine. In one embodiment, the method comprises measuring levels of RBC folic acid, 5-MTHF, THF, 5,10-MTHF, and any combination thereof in a biological sample. For example, a decrease in the levels of at least folic acid in the blood, serum, or plasma of the subject indicates that the subject's disease or condition is worsening. An increase in the levels of at lease folic acid in the blood, serum, or plasma of the subject indicates that the subject's disease or condition is improving.

Also provided are methods for evaluating the efficacy of therapeutic agents in subjects having a disease or condition associated with low folate status and elevated levels of homocysteine. The method comprises determining levels of any combination of RBC folic acid, 5-MTHF, THF, and 5,10-MTHF in a biological sample of the subject following treatment with the therapeutic agent. In one embodiment, levels of any combination of RBC folic acid, 5-MTHF, THF, and 5,10-MTHF is compared to levels of corresponding combination of RBC folic acid, 5-MTHF, THF, and 5,10-MTHF in the subject prior to treatment.

The method of measuring the levels of any combination of RBC folic acid, 5-MTHF, THF, and 5,10-MTHF in a biological sample includes using stable isotope dilution liquid chromatography, multiple reaction monitoring, mass spectrometry (LC/MRM/MS).

Also provided is a method to measure the levels and effects of folate antagonists.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease, rheumatoid diseases (e.g., rheumatoid arthritis), other arthritic diseases (e.g., acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, venereal arthritis, viral arthritis), fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis. Inflammatory bowel diseases are chronic inflammatory diseases of the gastrointestinal tract which include, without limitation, Crohn's disease, ulcerative colitis, and indeterminate colitis. Rheumatoid arthritis is a chronic inflammatory disease primarily of the joints, usually polyarticular, marked by inflammatory changes in the synovial membranes and articular structures and by muscle atrophy and rarefaction of the bones.

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjogren's syndrome, and multiple sclerosis.

The term "cancer" refers to any of various malignant neoplasms characterized by the proliferation of anaplastic cells that tend to invade surrounding tissue and metastasize to new body sites. Examples of different types of cancer include, but are not limited to, lung cancer, breast cancer, bladder cancer, thyroid cancer, liver cancer, pleural cancer, pancreatic cancer, ovarian cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, blood cancers, osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia.

Figure 6:
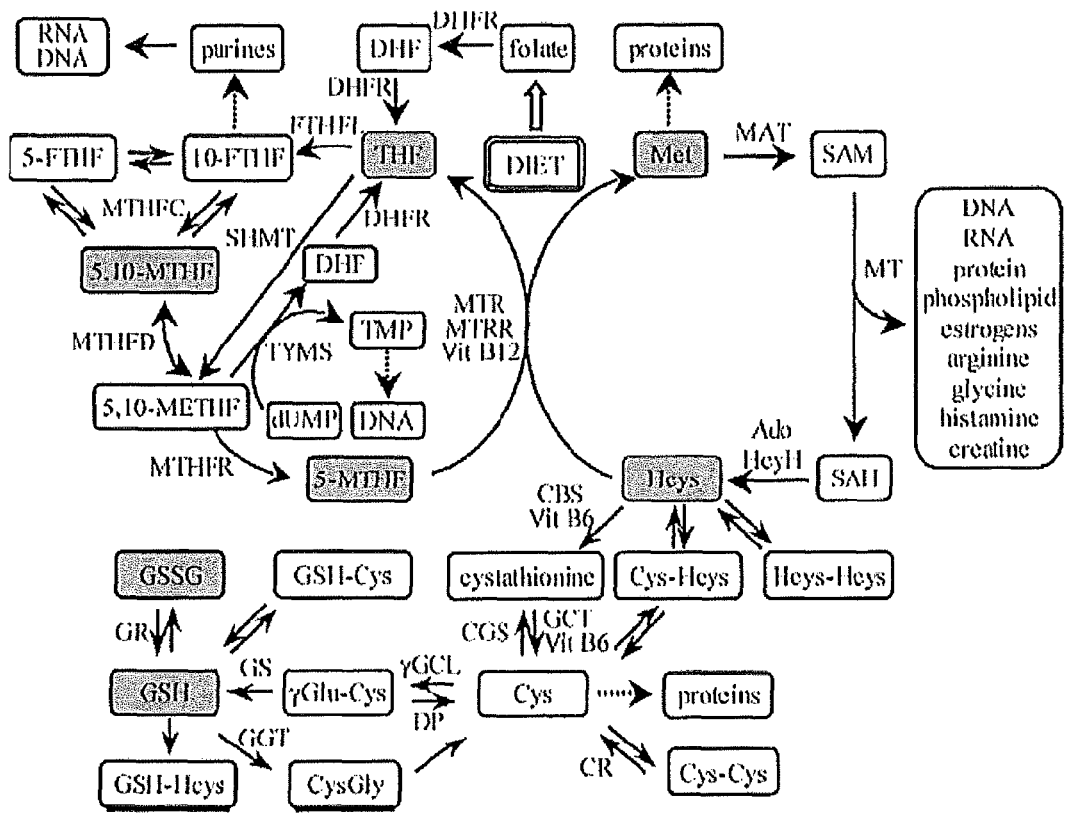
FIG. 6 is a schematic depicting the biochemical pathway of folate/homocysteine metabolism. Abbreviations used in FIG. 6 are as follows: BHMT=betaine homocysteine methyltransferase; CBL=cystathionine β-lyase; CBS=cystathionine β-synthase; CGS=cystathionine γ-synthase; CR=cysteine reductase; Cys=cysteine; DHFR=dihydrofolate reductase; DP=dipeptidases; dUMP=20-deoxyuridine monophosphate; FTHFL=formate tetrahydrofolate ligase; GGT=γ-glutamyl-transpeptidase; GGCL=γ-glutamylcysteinyl ligase; GR=glutathione reductase; GS=glutathione synthase; GSH=glutathione; Hcys=homocysteine; MAT=methionine adenosyltransferase; MTHFC=methylenetetrahydrofolate cyclohydrolase; MTHMD=methylenetetrahydrofolate dehydrogenase; MTHFD=methylenetetrahydrofolate reductase; MTR=methionine synthase; MTRR=methionine synthase reductase; SAH=S-adenosylhomocysteine; SAM=S-adenosylmethionine; SHMT=serine hydroxymethyltransferase; TMP=thymidine monophosphate; TYMS=thymidylate synthase; Vit=vitamin.

A "folate pathway gene" refers to any gene involved in folate homeostasis and/or metabolism and includes the proteins encoded by these genes. Examples of folate pathway genes include, but are not limited to, folate-dependent enzyme genes such as 5,10-methylenetetrahydrofolate reductase (MTHFR), 5-aminoimidazole-4-carboxamide ribonucleotide transformylase (ATIC), thymidylate synthase (TS), serine hydroxymethyltransferase (SHMT), dihydrofolate reductase (DHFR), 10-forrmyltetrahydrofolate synthetase (FTHFS), 10-formyltetrahydrofolate dehydrogenase (FTHFD), glycinamide ribonucleotide transformylase (GART), reduced folate carrier (RFC-1), folylpolyglutamate synthase (FPGS), gamma-glutamyl hydrolase (GGH), and combinations thereof; and homocysteine remethylation-dependent enzyme genes such as methionine synthase (MS), methionine synthase reductase (MTRR), betaine-homocysteine methyltransferase (BHMT), and combinations thereof. A schematic of the folate/homocysteine metabolism which modulates glutathione biosynthesis through the cystathionine/cysteine pathway is provided in FIG. 6.

As used herein, to "alleviate" a disease means reducing the severity of one or more symptoms of the disease.

A "disease" as used herein refers to a state of health of an animal wherein the animal cannot maintain homeostasis, and wherein if the disease is not ameliorated, then the animal's health continues to deteriorate.

A "disorder" as used herein refers to a state of health in which the animal is able to maintain homeostasis, but in which the animal's state of health is less favorable than it would be in the absence of the disorder. Left untreated, a disorder does not necessarily cause a further decrease in the animal's state of health.

The term "polymorphism" refers to the occurrence of two or more genetically determined alternative sequences or alleles in a population. A "polymorphic site" refers to the locus at which divergence occurs. Preferred polymorphic sites have at least two alleles, each occurring at a particular frequency in a population. A polymorphic locus may be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances," The alleles occurring most frequently in a selected population are sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

The term "genotype" refers to the genetic composition of an organism, including, for example, whether a diploid organism is wild-type, heterozygous, or homozygous for one or more variant alleles of interest.

The term "side-effect" refers to an undesirable secondary effect of a drug or therapy. For example, a typical side-effect associated with MTX therapy includes, but is not limited to gastrointestinal side-effect (e.g., nausea, diarrhea, stomatitis, dyspepsia), central nervous system side-effect (e.g., headache, lethargy), hematopoietie system side-effect (e.g., leucopenia, anemia), pulmonary system side-effect, alopecia, and combinations thereof.

The term "subject" or "patient" typically refers to humans, but also to other animals including, e.g., other primates, rodents, canines, felines, equines, ovines, porcines, and the like.

As used herein, the term "biomarker" or "marker" refers to any biochemical marker, serological marker, genetic marker, or other clinical or echographic characteristic that can be used in predicting or determining efficacy or toxicity in a subject according to the methods of the present invention. Examples of biochemical or serological markers include, but is not limited to derivatives of folate. Preferably, the biochemical or serological markers described herein are measured to determine their levels in a subject's sample. Examples of biochemical markers include, but is not limited to folic acid, 5-methyltetrahydrofolate (5-MTHF), tetrahydrofolate (THF), and 5,10-MTHF.

The term "sample" refers to any biological specimen obtained from a subject. Samples include, without limitation, whole blood, plasma, serum, buccal cells, red blood cells, white blood cells (e.g., peripheral blood mononuclear cells), neutraphils, saliva, urine, stool (i.e., feces), tears, any other bodily fluid, a tissue sample (e.g., tumor tissue) such as a biopsy of a tumor, and cellular extracts thereof. In certain instances, the sample is whole blood, serum, or plasma. In certain other instances, the sample is tumor tissue, e.g., from a solid tumor.

The term "folate polyglutamate" is synonymous with "folate PG" and refers to a derivative of folate having two or more glutamates which are bonded thereto via the action of folylpolyglutamate synthase. The number of glutamates in a folate polyglutamate varies from two to seven or more. For example, folate polyglutamates can include, without limitation, folate metabolites such as the pteroyldiglutamate, pteroyltriglutamate, pteroyltetraglutamate, pteroylpentaglutamate, pteroylhexaglutamate, and/or pteroylheptaglutamate forms of folate.

To "treat" a disease as the term is used herein, means to reduce the frequency of the disease or disorder reducing the frequency with which a symptom of the one or more symptoms disease or disorder is experienced by an animal.

Description

The invention provides a method to accurately identify and quantify forms of folate. Preferably, the method identifies and quantifies at least three key forms of folate that are present in different parts of folate/homocysteine metabolism. The method allows for the differential diagnosis and assessment of the risks associated with a particular pathology. The method also provides a means to predict and monitor responses to vitamin supplements (e.g., folic acid and other B vitamins) and anti-folate medications. The method also provides a means to predict and monitor responses to medications for inflammation and/or autoimmune diseases.

The present invention provides a method for detecting and quantifying the amount of any combination of RBC folic acid, 5-MTHF, THF, and 5,10-MTHF in a sample. The method also allows for the assessment of the relationship between different methylenetetrahydrofolate reductase (MTHFR) 677C>T genotypes and RBC folate phenotypes.

The invention also provides a method for screening an individual to determine if the individual is at increased risk of developing low folate status by determining the absolute amount of any combination of RBC folic acid, 5-MTHF, THF, and 5,10-MTHF in a sample. Alternatively, the ratio of RBC folic acid, 5-MTHF, THF, and 5,10-MTHF relative to each other in a sample can be used to determine the disease state or disease risk of the individual. Individuals found to be at increased risk can be given folic acid supplementation and subjected to more frequent monitoring for low folate status and hyperhomocysteinemia and for the various conditions (such as cardiovascular disease, stroke, and colon cancer) associated with these conditions. Additionally, premenopausal women can be given folk acid supplementation above the normal recommendations if pregnant, to reduce the risk that they will bear children with birth defects associated with folic acid deficiency. Therefore the invention is useful in monitoring levels of forms of folate before and/or after pregnancy.

Methods:

The present invention provides a method for detecting levels of folate in a biological sample. In one embodiment, the method included detecting key red blood cell folates in a biological sample using a type of mass spectrometry. Preferably, the type of mass spectorometry is in combination with using stable isotope dilution liquid chromatography, multiple reaction monitoring, mass spectrometry (LC/MRWMS). The measured folate derivatives are 5-MTHF, THF and 5,10-MTHF.

In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The sample may be pretreated as necessary by dilution in an appropriate buffer solution, heparinized, concentrated if desired, or fractionated by any number of methods. Any of a number of standard aqueous buffer solutions, employing one of a variety of buffers, such as phosphate, Tris, or the like, at physiological pH can be used.

The test sample also includes an isotopically enriched folate standard that has optionally been derivatized with the same reagent. The test sample is scanned using a mass spectrometer to produce one or more mass spectra. The level of folate in the test sample is determined by comparing a peak in the one or more mass spectra that corresponds to a type folate with a peak in the one or more mass spectra that corresponds to isotopically enriched folate. Optionally, the level of folate in the sample can then be determined based on the extraction efficiency of the extraction solution. If the level of folate in the test sample or blood sample is outside the range of normal folate levels then the blood sample or the patient from whom it was obtained may be referred for further analysis. Folate levels may also be measured in combination with liquid chromatograpy. The method provides quantification of types of red blood cell folates using a combination of isotope dilution liquid chromatography/mass spectrometry.

The method that embodies the invention is based on the application of stable isotope dilution liquid chromatography-multiple reaction monitoring/mass spectrometry LC-MRM/MS, under novel conditions of analyte preparation that permits the identification of 5-MTHF, THF, and 5,10-MTHF. However, measurement of the above forms of folate by methods that could be adapted from known art including but is not limited to antibody-based assays, radiometric assays, chromatographic methods, microbiological assays, and the like. The utility of a method for measuring the above three forms of folate, individually and together, as absolute values and as ratios relative to each other, is its prediction of concentrations of other biomarkers of disease state and disease risk. Another utility of the method includes prediction of disease state and response to therapy.

In one embodiment, the combination of RBC folic acid, 5-MTHF, THF, and 5,10-MTHF in a sample was quantified by initially analyzing for FA, THF, and 5-MTHF. Then the sample is acidified for analysis of the 5-METHF precursors as 5,10-MTHF. For example, an isotope-5-FTHF internal standard was quantitatively converted into isotope-5,10-MTHF, which enable for the accurate quantification for the amount of unlabeled 5-FTHF and 10-FTHF, as well as any 5,10-MTHF that had been in the sample originally. This step quantitatively measures the conversion of 5-FTHF and 10-FTHF into 5,10-MTHF and isotope-5-FTHF into isotope-5,10-MTHF analyzed by LC-MRM/MS. Other useful internal standards include isotope-FA, isotope-THF, and isotope-5-MTHF. Preferably, the isotope standards incldue $[^{13}C_5]$-FA, $[^{13}C_5]$-THF, $[^{13}C_5]$-5-MTHF, and $[^{13}C_5]$-5-FTHF.

In certain embodiments, the methods of the present invention comprise comparing levels of total RBC folic acid, 5-MTHF, THF, and 5,10-MTHF in a sample obtained from the test subject to levels of total RBC folic acid, 5-MTHF, THF, and 5,10-MTHF in a sample obtained from subjects lacking the disease, i.e., healthy or normal subjects. Alternatively, levels of total RBC folic acid, 5-MTHF, THF, and 5,10-MTHF in a sample may be compared to levels of total RBC folic acid, 5-MTHF, THF, and 5,10-MTHF in corresponding samples which were taken from the test subject for the purpose of determining baseline levels of the diagnostic marker.

In some instances, the method includes discrimination between the forms of folate (e.g., RBC folio acid, 5-MTHF, THF, and 5,10-MTHF), thereby permitting refinement of disease diagnosis, disease risk prediction, and clinical management of patients being treated with anti-folate therapies. That is, the ratio of RBC folic acid, 5-MTHF, THF, and 5,10-MTHF is used as a marker for the disease state or disease risk. For example, discrimination between key forms of folate permits refinement of disease diagnosis, disease risk prediction, and clinical management of patients being treated with anti-folate therapies.

Levels of RBC folio acid, 5-MTHF, THF, and 5,10-MTHF in a sample of the test subject may be compared to a control value that is derived from levels of RBC folk acid, 5-MTHF, THF, and 5,10-MTHF in a sample in comparable samples of control subjects. The control value can be based upon levels of RBC folic acid, 5-MTHF, THF, and 5,10-MTHF in comparable samples obtained from the general population or from a select population of human subjects. For example, the select population may be comprised of apparently healthy subjects. "Apparently healthy", as used herein, means individuals who have not previously had any signs or symptoms indicating the presence of disease, and/or evidence of disease by low folate status and associated elevated levels of homocysteine. In other words, such individuals, if examined by a medical professional, would be characterized as healthy and free of symptoms of hyperhomocyteinemia. In an alternative embodiment, levels of RBC folic acid, 5-MTHF, THF, and 5,10-MTHF in the test sample may be compared to an internal standard based on total levels of RBC folic acid, 5-MTHF, THF, and 5,10-MTHF in the subject's biological sample.

Also provided herein are methods for monitoring over time the status of RBC folk acid, 5-MTHF, THF, and 5,10-MTHF (and/or analogous disease or condition) in a subject. In one embodiment, the method comprises determining the levels of one or more of RBC folic acid, 5-MTHF, THF, and 5,10-MTHF in a sample in a biological sample taken from the subject at an initial time and in a corresponding biological sample taken from the subject at a subsequent time. A decrease in levels of RBC folic acid, 5-MTHF, THF, and 5,10-MTHF in a biological sample taken at the subsequent time as compared to the initial time indicates that the severity of the subject's hyperhomocysteinemia has increased. An increase in levels of RBC folic acid5-MTHF, THF, and 5,10-MTHF in a sample indicates that the severity of the subject's hyperhomocysteinemia has decreased.

In another embodiment, the present invention provides a method for characterizing a subject's response to anti-inflammatory agents therapy directed at stabilizing or regressing hyperhomocysteinemia and/or an analogous disease associated with increased levels of homocysteine and low folate. Examples of such anti-inflammatory agents include, but are not limited to, steroids and immunomodulating drugs (e.g., methotrexate; MTX), cytokine antagonist (e.g., Embrel). In one embodiment, the method comprises determining levels of RBC folic acid, 5-MTHF, THF, and 5,10-MTHF in a subject prior to therapy and determining levels of RBC folic acid, 5-MTHF, THF, and 5,10-MTHF in the subject during or following therapy.

In some instances, the levels of RBC folic acid, 5-MTHF, THF, and 5,10-MTHF are optionally used in conjunction with Hcy measurements, to mitigate the side effects of drugs with anti-folate properties (e.g., MTX and 5-fluorouracil (5-FU)), to determine whether folic acid supplements should be prescribed/recommended to correct deficiency/insufficiency, and to reduce the risk of cardiovascular disease, birth defects and other pathologies.

The method of the invention is useful for as a patient management tool for example in arthritis patients being treated with methotrexate (MTX) for evaluating the levels of folates in the subject. Part of the unpredictability of side-effects associated with MTX therapy may be related to common polymorphisms in genes implicated in MTX pharmacokinetics or pharmacodynamics. A genetic marker associated with MTX toxicity in patients (e.g., with rheumatoid arthritis) is a common polymorphism in 5,10-methylenetetrahydrofolate reductase, MTHFR C677T. Accordingly, the invention allows for monitering the toxicity of MTX therapy by way of assessing the levels of at least 5-MTHF, THF, and 5,10-MTHF in the subject.

The liquid chromatograpy-multiple reaction monitoring/mass spectrometry (LC-MRM/MS) method of the invention for quantitative determination of RBC folic acid, 5-MTHF, THF and 5,10-MTHF allows for a robust, accurate, validated assay that is applicable to plasma and RBCs from human subjects. The method provides assessing Folate/Hcy phenotypes in the context of functional genetic polymorphisms of folate metabolizing enzymes that are, themselves, known to influence folate/homocysteine phenotype. The invention also provides a method to assess the relationships between the phenotypes and circulating concentrations of an important pro-inflammatory hormone, the chemokine monocyte chemoattractant protein-1 (MCP-1). The phenotypes can be used to identify subsets of individuals within particular folate genotype classes who have different characteristics with respect to disease risk and response to anti-folate therapy. An example of genes associated with disease state includes enzymes whose deficiency may raise plasma homocysteine such as methylenetetrahydrofolate reductase (MTHFR), methionine synthase, and folate receptors/transport proteins/binding proteins.

The present invention therefore provides methods for: (a) Diagnostic testing of disease state by identifying levels of folate; (b) prevention of disease by diagnostic testing in families already affected by diagnostic screening for levels of folate; and (c) therapy, e.g., treating the individual with folate or other agents. The treatment can be monitored at regular intervals to determine the effect of therapy with respect to the level of 5-MTHF, THF, and 5,10-MTHF.

In one embodiment, the invention allows for predicting the levels of hymocysteine concentrations with enhanced precision by determining the levels of RBC folic acid, 5-MTHF, THF, and 5,10-MTHF.

In one embodiment, THF levels predict elevated monocyte chemoattractant protein −1 (MCP-1) concentrations. Altered MCP-1 expression is believed to influence the risk of neural tube defect (NTD) through modulation of maternal inflammatory responses. Thus, the invention provides a diagnostic tool for assessing NTD risk.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Example 1

Quantification of Key Red Blood Cell Folates

Red blood cell (RBC) folate levels are established at the time of erythropoiesis and therefore provide a surrogate biomarker for the average folate status of an individual over the preceding four months. Folates are present as folylpolyglutamates, highly polar molecules that cannot be secreted from the RBCs, and must be converted into their monoglutamate forms prior to analysis. This was accomplished using an individual's plasma pteroylpolyglutamate hydrolase by lysing the RBCs in whole blood at pH 5 in the presence of ascorbic acid. Quantitative conversion of formylated tetrahydrofolate derivatives into the stable 5,10-methenyltetrahydrofolate (5,10-MTHF) form was conducted at pH 1,5 in the presence of [$^{13}C_5$]-5-formyltetrahydrofolate. The resulting [$^{13}C_5$]-5,10-MTHF was then used as an internal standard for the formylated forms of tetrahydrofolate that had been converted into 5,10-MTHF as well as any 5,10-MTHF that had been present in the original sample. A stable isotope dilution liquid chromatography-multiple reaction monitoring/mass spectrometry method was validated and then used for the accurate and precise quantification of RBC folic acid, 5-MTHF, THF, and 5,10-MTHF.

The results presented herein demonstrate that the method of the invention was sensitive and robust and was able to be used to assess the relationship between different ethylenetetrahydrofolate reductase (MTHFR) 677C>T genotypes and RBC folate phenotypes. Four distinct RBC folate phenotypes were identified. These were classified according to the relative amounts of individual RBC folates as type I (5-MTHF>95%; THF<5%; 5,10-MTHF<5%), type II (5-MTHF<95%; THF 5% to 20%; 5,10-MTHF<5%), type III (5-MTHF>55%; THF>20%; 5,10-MTHF>5%), and type IV (5-MTHF<55%; THF>20%; 5,10-MTHF>5%).

The results presented herein demonstrate the succesful development of a validated stable isotope dilution LC-MRM/MS method for the analysis of RBC and plasma folates and its use to identify different phenotypes between and within the MTHFR 677C>T homozygous CC, heterozygous CT, and homozygous TT genotypes. The invention is an advancement to the various methodology that exist for folate analysis (Quinlivan et al., 2006, Anal. Biochem. 348(2);163-84), including microbiological (Molloy et al., 1997, Methods Enzymol. 281:43-53; Molloy et al., 1997, Lancet 349(9065): 1591-3), competitive binding assays (radioassays) (Molloy et al., 1997, Lancet 349(9065):1591-3; McGown et al., 1978,. Clin. Chem. 24(12):2186-91), liquid chromatography (LC)/electrochemical detection (Lucock et al., 1989, Biomed. Chromatogr. 3(2):58-63; Bagley et al., 2000, J. Clin. Chem. 46(3);404-11), LC/fluorescence (Freisleben et al., 2003, Anal. Biochem. 315(2):247-55), gas chromatography/mass spectrometry (GC/MS) (Santhosh-Kumar et al., 1995, Anal. Biochem. 225(1):1-9; Santhosh-Kumar et al., 1997, Eur. J. Clin. Nutr. 51(3):188-92), and LC-multiple reaction monitoring (MRM)/MS (Botto et al., 2000, Am. J. Epidemiol. 151 (9):862-77; Garbis et al., 2001, Anal. Chem, 73(22):5358-64; Pfeiffer et al., 2004, Clin. Chem. 50(2):423-32; Fazili et al., 2004, Clin. Chem, 50(12):2378-81; Owens et al., 2005, J. Agric. Food Chem. 53(19):7390-4; Fazili et al., 2005, Clin. Chem. 51(12):2318-25; Nelson et al., 2005, Anal. Chem. 77(10:3586-93; Satterfield et al., 2006, Anal. Bioanal. Chem 385(3):612-22; Smith et al., 2006, Clin. Chem. Lab Med. 44(4):450-9; Owens et al., 2007, J. Agric. Food Chem. 55(9): 3292-7; Fazili et al., 2008, Clin. Chem. 54(1):197-201; Ueland et al., 2007, Clin. Chem. Lab. Med. 45(12):1737-45). This is because many of the available methods have limited utility for rigorous population studies attributed to the ease with which RBC folates can degrade and/or interconvert during the analytical procedure. The present invention utilizes a methodology based on stable isotope dilution LC-MRM/MS, which can efficiently correct for such problems. Specificity is conferred by requirements that the folates must have the same LC retention time as their corresponding [$^{13}C_5$]-labeled internal standards, as well as the same precursor ion and the same product ion as authentic unlabeled standards. Prior art methods cannot provide this level of specificity. Prior to the present invention, no prior art method has been validated for quantification of the key RBC folates in human subjects with well-defined genotypes.

The materials and methods employed in the experiments disclosed herein are now described.

Materials Supelco LC-18 3 mL solid-phase extraction (SPE) cartridges were obtained from Supelco (Bellefonte, Pa., USA). HPLC grade water, methanol, and acetonitrile were obtained from Fisher Scientific Co, (Fair Lawn, N.J., USA). 2-Mercaptoethanol was obtained from Bio-Rad Laboratories (Hercules, Calif., USA). Folic acid (FA), THF, 5-MTHF, acetic acid, and ascorbic acid were purchased from Sigma-Aldrich (St. Louis, Mo., USA). 5,10-MTHF, 5,10-methylenetetrahydrofolic acid (METHF), 5-formyltetrahydrofolic acid (5-FTHF), 10-formyltetrahydrofolic acid (10-FTHF) and pteroylhepta-γ-L-glutamic acid were obtained from Schircks Laboratories (Jona, Switzerland). [$^{13}C_5$]-FA, [$^{13}C_5$]-THF, [$^{13}C_5$]-5-MTHF, and [$^{13}C_5$]-5-FTHF were obtained from Eprova AG (Schafhausen, Switzerland). Argon and liquid nitrogen were obtained from BOC Gases (Bellmawr, N.J., USA).

Samples from Individuals with Defined MTHFR 677C>T Genotypes

Blood samples were obtained from female subjects enrolled in two ongoing studies of folate and homocysteine metabolism at the University of Pennsylvania School of Medicine. Major exclusionary criteria for the studies were use of anti-folate medications and pregnancy. Both studies were approved by the Institutional Review Board of the University of Pennsylvania School of Medicine, and all subjects gave written informed consent. The samples used were from the first five Caucasian subjects under the age of 50 years in each of the MTHFR 677C>T genotype classes (i.e., CC, CT, and TT) who had been recruited for each of the studies.

Whole Blood Samples

Blood samples for RBC folate analysis were drawn into 4M1 EDTA (purple top) tubes and placed in the dark until processed. Each tube was gently inverted (without shaking or foaming contents) six times prior to transfer of 1 mL aliquots to separate 15 mL tubes and addition of 9 mL aqueous 1% ascorbic acid solution.[20,40] Each tube was gently inverted six times, left in the dark at room temperature for 30 min, and then gently inverted six more times. Contents were transferred to dark amber 2 mL tubes, frozen on dry ice, and stored at −80° C. until analyzed.

Plasma Samples

Blood samples for plasma folate analysis were drawn into 4 mL EDTA (purple top) tubes and placed in the dark until processed. The tubes were centrifuged in a Eurotech (Beaconsfield, UK) Z-150 A centrifuge at 1100 g for 5 min. The resulting plasma was transferred to dark amber 2 mL tubes, frozen on dry ice and stored at −80° C. until analyzed.

DNA Isolation and MTHFR 677C>T Genotyping

DNA was extracted from whole blood using the QIAamp@ DNA Mini Kit (Qiagen). MTHFR 677C>T (rs1801133) allelic discrimination was performed using a TaqMan 50 Nuclease real-time polymerase chain reaction (PCR) assay on a DNA Engine Opticon 2 continuous fluorescence detection system (MJ Research, Waltham, Mass., USA). PCR amplification was performed using 2 μL of sample DNA, 1× TaqMan Universal PCR MasterMix (Applied Biosystems, Foster City, Calif., USA), 0.5 μM of each primer (5'-GCAGG-GAGCTTTGAGGCTGACC-3'; SEQ ID NO: 1 and 5'-TGGGGCAAGTGATGCCCATGT-3'; SEQ ID NO: 2), 50 nM 'T'-specific probe (6FAM-ATGAAATCGACTCCCGC-MGBNFQ; SEQ ID NO: 3) and 100 nM 'C'-specific probe (VIC-ATGAAATCGGCTCCCGC-MGBNFQ; SEQ ID NO: 4). Probe sequences were derived from the SNP500Cancer website. They were custom synthesized by Applied Biosystems (Foster City, Calif., USA). PCR was performed with an initial incubation at 95° C. for 10 min, followed by 60 cycles of denaturation at 92° C. for 30 sec and extension/50 nuclease step at 56° C. for 1 min. Dual fluorescence was detected after each extension 50 nuclease step. Genotype interpretations were performed using OpticonMonitor Analysis software version 2.02 (MJ Research, Ramsey, Minn., USA).

Preparation of Standard and QC Solutions

All procedures were performed under conditions of decreased laboratory lighting. Standards and quality control (QC) solutions were prepared using certified volumetric flasks with certified Hamilton microsyringes. Stock solution I for 5-MTHF, 5-FTHF, and THF (100 μg/mL) was prepared by dissolving 5-MTHF (1 mg, 2.2 μmol), 5-FTHF (1 mg, 2.1 μmol) and THF (1 mg, 2.2 μmol) in 20 mM phosphate buffer (pH 7.2) containing cysteine (1 mg/mL) in a 10 mL volumetric flask. Phosphate buffer was added to the mark, an aliquot (200 μL) of the solution was removed for ultraviolet (UV) spectrophotometry using a Beckman Du530 UV spectrophotometer (Beckman Instruments, Fullerton, Calif., USA), and ascorbic acid (100 mg) was then added to the volumetric flask. Stock solution I for FA (100 μg/mL; 1 mg, 2.3 μmol) was prepared in a similar manner, except that 20 mM phosphate buffer (pH 7.2) was used without the addition of cysteine or ascorbic acid, and an aliquot (200 μL) was removed for UV analysis. Concentrations of each folate were determined after a 20-fold dilution with phosphate buffer (5-MTHF $\lambda_{max}$=290 nm ε=31.7 L/mmol/cm; 5-FTHF $\lambda_{max}$=285 nm ε=37.2 L/mmol/cm; THF $\lambda_{max}$=297 nm ε=29.1 L/mmol/cm; FA $\lambda_{max}$=282 nm ε=27.6 L/mmol/cm).[42] Stock solution I for 5,10-MTHF (100 μg/mL; 1 mg, 2.2 μmol) was prepared in a similar manner except that it was dissolved in 5 mM hydrochloric acid. The concentration was confirmed using a 20-fold dilution with 0.01% acetic acid at pH 3 (5,10-MTHF $\lambda_{max}$=360 nm ε=25.1 L/mmol/cm) (Blakely RL. The biochemistry of folic acid and related pteridines. In Frontiers of Biology, Neuberger A, Tatum EL (eds). North Holland: London, 1969; 92). All the standards and QC samples were prepared by serial dilutions from these stock solutions. Working solutions were prepared every 4 weeks and their concentrations were checked by UV spectrophotometry before use. Heavy isotope standard solutions were prepared in the same way as the relevant unlabeled folate standards.

Mass Spectrometry

Mass spectrometry was conducted using an Applied Biosystems API4000 triple-quadrupole mass spectrometer (Foster City, Calif., USA) equipped with a turboionspray source and operated in the positive ion mode. Operating conditions were as follows: source temperature, 450° C.; spray voltage, 5.0 kV; collision cell exit potential, 10V; collision gas pressure, 6 psi; curtain gas, 30 psi; Gas1, 40 psi; and Gas2, 30 psi. LC-MRM/MS was conducted using the following transitions for FA, m/z 442 (MH$^+$) to m/z 295 (MH$^+$-γ-glutamate); [$^{13}C_5$]-FA, m/z 447 (MH$^+$) to m/z 295 (MH$^+$-γ-glutamate); THF, m/z 446 (MH$^+$) to m/z 299 (MH$^+$-γ-glutamate); [$^{13}C_5$]-THF, m/z 451 (MH$^+$) to m/z 299 (MH$^+$-γ-glutamate); 5-MTHF, m/z 456 (M$^+$) to m/z 412 (M$^+$-CO$_2$); [$^{13}C_5$]-5-MTHF, m/z 461 (M$^+$) to m/z 416 (M$^+$-CO$_2$); 5,10-MTHF, m/z 456 (MH$^+$) to m/z 412 (MH$^+$-CO$_2$); [$^{13}C_5$]-5,10-MTHF, m/z 461 (MH$^+$) to m/z 416 (MH$^+$-CO$_2$); 5-FTHF m/z 474 (MH$^+$) to m/z 327 (MH$^+$-γ-glutamate); [$^{13}C_5$]-5-FTHF m/z 479 (MH$^+$) to m/z 327 (M$^+$-γ-glutamate). Collision offset energies for FA, THF, 5-MTHF, 5,10-MTHF, and 5F-THF were 21, 29, 27, 41, and 29V, respectively.

Liquid Chromatography

Chromatography was performed using an Agilent 1100 separation module (Palo Alto, Calif., USA) equipped with a Leap autoinjector (CTC Analytics AG, Switzerland). Gradient elution of the folates was conducted in the linear mode using a YMC ODS-AQ column (150×2.0 mm i.d., 3 μm, 120 Å Waters Inc., Milford, Mass., USA). Mobile phase A was 1% acetic acid in water and mobile phase B was 1% acetic acid in methanol/acetonitrile (4:1). The flow rate was 200 μL/min. The gradient conditions were as follows: 0 min, 1% B; 10 min, 91% B; 13 min, 91% B; 14 min, 1% B, and 25 min 1% B. The samples (2004) were maintained at 4° C. in the autosampler tray, and injections of 50 μL were made. The gradient was started immediately after the sample injection. The column effluent was diverted to waste for the first 8 min of the analysis to prevent extraneous and endogenous materials from entering the mass spectrometer.

Whole Blood Sample Preparation for RBC Folate Analysis

Eight calibration standards were prepared in the range 4.5 to 900 nmol/L in 1% ascorbic acid and 10 mM 2-mercaptoethanol (to prevent oxidation). To 500 μL of whole blood (1:10 diluted with 1% ascorbic acid) was added 20 μL of internal standard solution (150 pg/μL each of [$^{13}C_5$]-FA, [$^{13}C_5$]-THF, [$^{13}C_5$]-5-MTHF, and [$^{13}C_5$]-5-FTHF). For hydrolysis of folylpolyglutamates, 1N sodium hydroxide (6 μL) was added to each tube to adjust the pH to 5.0 and the samples were mixed immediately. In selected experiments, pteroylhepta-γ-L-glutamic acid (5 ng) was added to replicate (n-5) RBC preparations from five different subjects in order to monitor the efficiency of folylpolyglutamate hydrolysis. Samples were degassed with argon, which was also used to flush the tubes. The covered samples were kept at room temperature for 4 h in the dark in order to complete the hydrolysis of the polyglutamated forms of the folates. Before further purification using SPE columns, 1 mL water containing 1% ascorbic acid and 1% methanol was added.

Sample Preparation for Analysis of Plasma Folates

To each plasma sample (300 μL) was added water (200 μL) containing 1% ascorbic acid and 10 mM 2-mercaptoethanol. After the addition of 20 μL internal standard solution (150 pg/μL each of [$^{13}C_5$]-FA, [$^{13}C_5$]-THF, [$^{13}C_5$]-5-MTHF, and [$^{13}C_5$]-5-FTHF) the samples were thoroughly mixed. Water (1 mL) containing 1% ascorbic acid and 1% methanol was added prior to purification using SPE columns.

Solid-Phase Extraction

Supelco LC-18 3 mL SPE cartridges were conditioned with 1 mL methanol, which was followed by 1 mL of SPE buffer. After loading the sample (1.5 mL), the cartridge was washed with SPE buffer (2 mL) followed by 0.5 mL eluting buffer (60% methanol and 0.2% ascorbic acid). 1 mL eluting buffer was used to elute folates from the cartridge. The eluate was evaporated under nitrogen and re-dissolved in eluting water (200 μL). After centrifugation for 5 min at 12000 rpm an aliquot (50 μL) was analyzed for THF, 5-MTHF, and FA by LC-MRM/MS.

Conversion of 5-FTHF and 10-FTHF into 5,10-MTHF

After analyzing THF, 5-MTHF, and FA, 1M HCl (40 μL) was added to each vial and the sample was kept room temperature for 4 hour. This resulted in quantitative conversion of 5-FTHF and 10-FTHF into 5,10-MTHF and [$^{13}C_5$]-5-FTHF into [$^{13}C_5$]-5,10-MTHF. An aliquot of the resulting solution (50 μL) was then analyzed by LC-MRM/MS.

Validation Study

The validation study was performed (n=5) on the QC samples. The lower limit of quantitation (LLOQ) QC samples were 4.4, 4.5, 4.4, 4.5 nmol/L for 5-MTHF, THF, 5,10-MTHF, and FA, respectively. The lower QC (LQC) samples were 10.9, 11,2, 11.0, 11.3 nmol/L for 5-MTHF, THF, 5,10-MTHF, and FA, respectively. The middle QC (MQC) samples were 43.5, 44.9, 43.8, 45.3 nmol/L for 5-MTHF, THF, 5,10-MTHF, and FA, respectively. The high QC (HQC) samples were 174.1, 179.6, 175.3, 181.2 nmol/L for 5-MTHF, THF, 5,10-MTHF, and FA, respectively. The upper QC (UQC) sample was 870.6 nmol/L for 5-MTHF only.

Replicate Analysis of RBC Folates

Whole blood and plasma folates from five subjects were each analyzed five times using the methods described elsewherein and RBC folate concentrations determined. A separate whole blood and plasma sample from one subject was analyzed in duplicate on 15 separate occasions over a 1-year period in order to determine the precision of the assay over time and the stability of samples stored at −80° C.

Data Analysis

All data analysis was performed using Analyst software, version 1.41 (Concord, ON, Canada) from raw mass spectral data. Calibration curves were plotted using a linear regression with weighting index of 1/x. Concentrations of folates in validation samples were determined from the calibration line, and used to calculate the accuracy and precision of the method within the study.

Calculation of RBC Folate Concentrations

RBC folate concentrations were calculated according to the method of Lamers et al.(2006, Am. J. Clin. Nutr. 84(1): 156-61):

RBC folate={(whole blood folate×100)−[plasma folate×(100−hematocrit)]}/hematocrit.

The results from the experiments are now discussed.

Conversion of 5-FTHF and 10-FTHF into 5,10-MTHF

5-FTHF and 10-FTHF undergo dehydration to 5,10-MTHF under acidic conditions in a pH-dependent manner (FIG. 1). In contrast, under neutral or alkaline pH conditions, 5,10-MTHF is converted into 10-FTHF, which then slowly interconverts with 5-FTHF. These different forms of folate are present in RBCs primarily in polyglutamated forms. It is common practice to initiate hydrolysis via activation of human plasma pteroylpolyglutamate hydrolase by lysing the RBCs under acidic conditions (pH 5) in the presence of ascorbic acid (Quinlivan et al., 2006, Anal. Biochem. 348(2):163-84; Pfeiffer et al., 1996, Clin. Chem, 42(11):1847-54). Therefore, there is always some conversion of 5-FTHF and 10-FTHF into 5,10-MTHF. The alternative use of rodent serum pteroylpolyglutamate hydrolases with isolated lysed RBCs still requires an acidic pH for optimal activity (Thomas et al., 2003, J. Agric. Food Chem 51(5):1293-6). This made it difficult to reliably quantify the individual amounts of 5-FTHF, 10-FTHF, and 5,10-MTHF in the RBCs. Conversion of 5-FTHF and 10-FTHF into 5,10-MTHF proceeded quantitatively at pH 1.5. As a result, it was possible to accurately quantify the pool of folate precursors available for conversion into 5,10-METHF simply by acidifying the RBC extract (FIG. 1). Unfortunately, under these conditions, THF was unstable. Therefore, samples were analyzed initially for FA, THF, and 5-MTHF. They were then acidified to pH 1.5 with 1M HCl ready for analysis of the 5-METHF precursors as 5,10-MTHF (FIG. 1). The [$^{13}C_5$]-5-FTHF internal standard was quantitatively converted into [$^{13}C_5$]-5,10-MTHF, which made it possible to accurately quantify the amount of unlabeled 5-FTHF and 10-FTHF, as well as any 5,10-MTHF that had been present in the sample originally. By monitoring the MRM channels for [$^{13}C_5$]-5-FTHF, as well as unlabeled 5-FTHF, and 10-FTHF, it was also possible to ensure that quantitative conversion into 5,10-MTHF had occurred (data not shown), 5,10-METHF is extremely unstable under both acidic and basic conditions and so it is not possible to analyze this form of folate in RBCS. However, it is so rapidly utilized in cellular processes by enzymes such as MTHFR, serine hydroxymethyltransferase, and thymidylate synthase (FIG. 6) that it is unlikely to be present in significant quantities.

LC/MS

Figure 2:
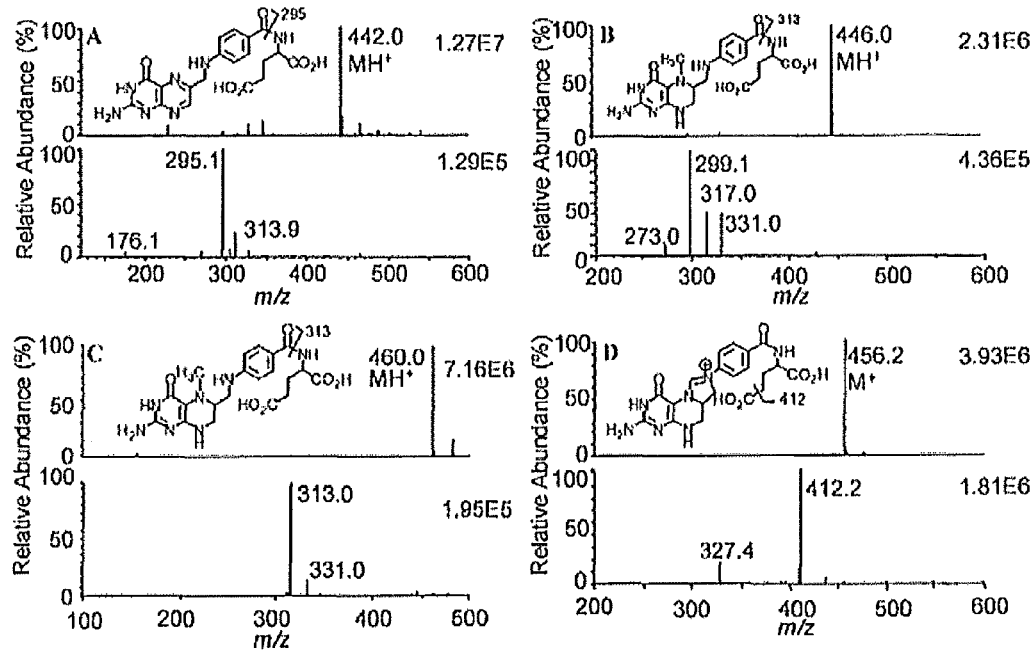
FIG. 2, comprising
Figure 3:
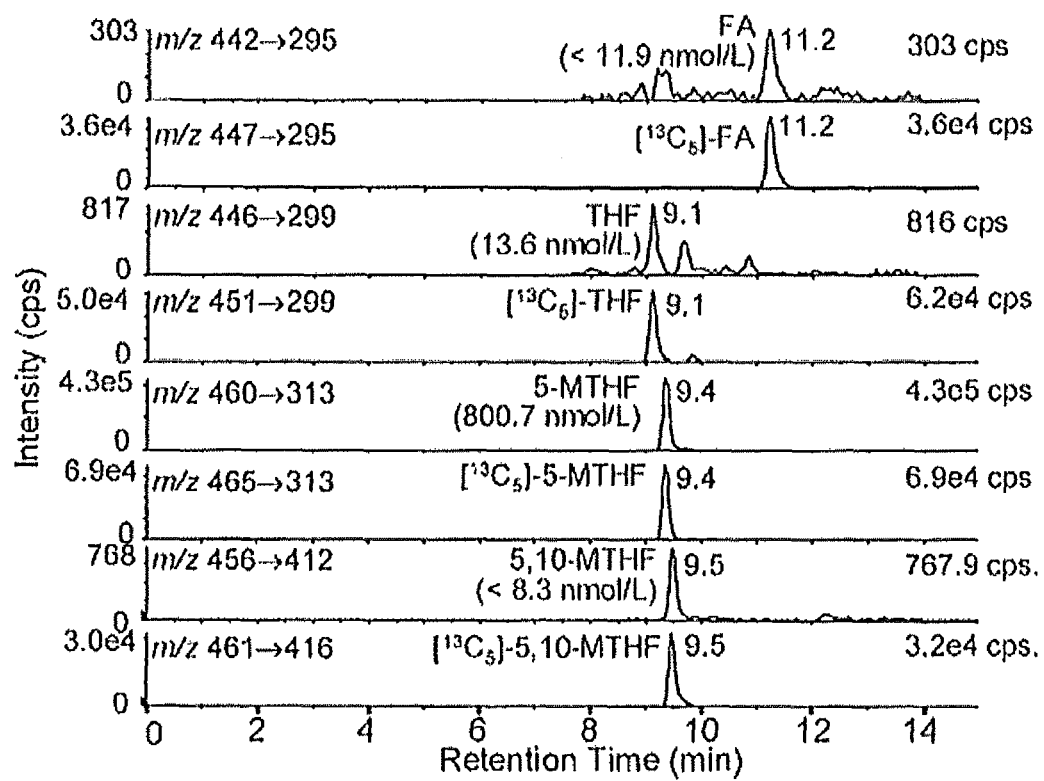
FIG. 3 is an image depicting LC-MRM/MS chromatograms of RBC folates from a homozygous MTHFR 677CC genotype that was a type 1 phenotype (5-MTHF>95%; THF<5%; 5,10-MTHF<5%).
Figure 4:
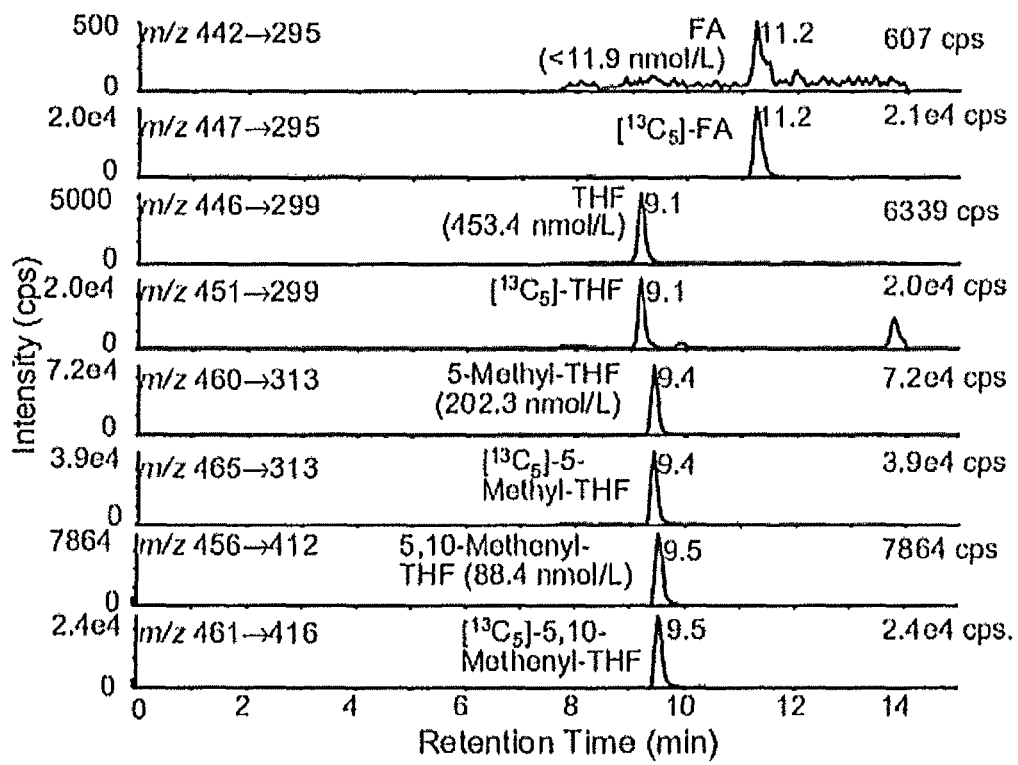
FIG. 4 is an image depicting LC-MRM/MS chromatograms of RBC folates from a homozygous MTHFR 677TT genotype that was a type IV phenotype (5-MTHF<55%; THF>20%; 5,10-MTHF>5%).

Under positive turboionspray conditions, the most abundant folate ions arose from the protonated molecules (MH$^+$), except for 5,10-MTHF, which is already charged (M$^+$). In the full scan mode, FA, THF, 5-MTHF, and 5,10-MTHF had precursor ions at m/z 442, 446, 460, and 456, respectively (FIGS. 2(A)-2(D)). The most abundant product ions observed for FA, THF, and 5-MTHF after collision-induced dissociation and MS/MS analysis corresponded to loss of the g-glutamate residue (FIGS. 2(A)-2(C)). On the other band, the product ion corresponding to loss of the carboxyl group was the major product ion observed for 5,10-MTHF (FIG. 2(D)). Formic acid, acetic acid, and trifluoroacetic acid were tested as mobile phase additives to improve chromatographic peak shape and MS signal. Acetic acid (1%) gave the highest ion intensities so it was chosen for the folate analyses. Several columns were also tested in order to improve the separation of individual folates from any endogenous interfering signals. Excellent separations were observed using the cyanopropyl column; however, substantial peak tailing occurred. In contrast, the YMC C18 AQ column separated each of the folates and gave excellent peak shapes (FIGS. 3 and 4). Retention times were between 9 and 12 min.

Hydrolysis Efficiency

Pteroylhepta-γ-L-glutamic acid was used to examine the hydrolysis efficiency of plasma pteroylpolyglutamate hydrolase in the pH range 4.0 to 7.0, As described previously (Quinlivan et al., 2006, Anal. Biochem. 348(2):163-84), optimal hydrolysis occurred at pH 5 (data not shown). Replicate (n=5) RBC preparations from five different subjects were then spiked with pteroylhepta-γ-L-glutamic acid, in order to monitor the efficiency of plasma human pteroylpolyglutamate hydrolase-mediated conversion of folylpolyglutamates into the corresponding monoglutamates. This approach was reported previously by Pfeiffer and Gregory for determining the hydrolysis efficiency of pteroylpolyglutamate hydrolase except that pteroylhepta-γ-L-glutamic acid was used instead of 5-MTHF-hepta-γ-Lglutamic acid (Pfeiffer et al., 1996, Clin. Chem. 42(11):1847-54). In the present samples, the hydrolysis efficiency was 98.7±7.2% (n=25).

Sensitivity and Linearity

To determine the limit of detection (LOD), a serial dilution of folate was prepared (0.1 to 10 ng/mL). The LOD determined at a signal/noise (SIN) ratio of 3:1 for FA, THF, 5-MTHF, and 5,10-MTHF were 3, 6, 2.5, and 1.2 pg on-column, respectively. Sensitivities were similar to those reported recently.[36] Calibration curves were prepared in the range of 4.5 to 900 nmol/L. Samples were stored in 1% ascorbic acid containing 10 mM 2-mercaptoethanol. Calibration curves for FA (y=0.0109x −0.0008; $r^2$ 0.9999), THF (y=0.0070x −0.0052; $r^2$ 0.9999), 5-MTHF (y=0.0427x −0.0652; $r^2$ 0.9996), and 5,10-MTHF (y=0.0183x −0.0442; $r^2$ 0.9973) were fitted to a linear regression with a 1/x weighting.

Accuracy and Precision

Concentrations of folates in QC samples were determined from the calibration line on each occasion and are presented in Table 1 along with accuracy and precision values. At all QC sample concentrations examined, the accuracy was well within 100±15% and the precision values were better than 15%. These criteria meet the guidelines on bioanalytical methods validation recommended by the FDA-sponsored meeting in Crystal City, Va. in 2006 (Chaudhary et al., 2006 Am. Drug Discov. 1: 34). RBC samples from five individuals were each analyzed as five replicates, and again acceptable precision and accuracy were obtained (Table 2). Generally, 5-MTHF was the dominant form of folate in RBCs with much smaller amounts of THF and 5,10-MTHF (Table 2). Finally, an RBC sample from a single individual was analyzed in duplicate on 15 separate occasions over a 1-year period. 5-MTHF values were 1120.0±46.6 nmol/L (coefficient of variance (CV) 4.2%), THF values were 26.2±3.1 nmol/L (CV 11.8%), and 5,10-MTHF concentrations were 6.0±52.3 nmol/L (CV 11.4%). Therefore, the assay was robust and long-term storage of the samples did not result in any deterioration of the individual RBC folates.

TABLE 1

Precision and accuracy of folate analyses (n = 15)

| Analyte | Parameter | LLOQ (nmol/L) | LQC (nmol/L) | MQC (nmol/L) | HQC (nmol/L) | UQC (nmol/L) |
|---|---|---|---|---|---|---|
| FA | Mean | 4.8 | 11.3 | 44.6 | 179.7 | |
| | Precision (%) | 8.7 | 2.7 | 3.0 | 2.9 | |
| | Accuracy (%) | 102.8 | 100.2 | 98.3 | 99.1 | |
| 5-MTHF | Mean | 4.4 | 10.7 | 41.8 | 169.3 | 850.6 |
| | Precision (%) | 4.1 | 3.5 | 5.2 | 3.7 | 3.3 |
| | Accuracy (%) | 98.4 | 97.5 | 96.1 | 97.3 | 97.7 |
| THF | Mean | 4.7 | 11.4 | 44.7 | 178.5 | |
| | Precision (%) | 13.9 | 8.5 | 5.9 | 5.0 | |
| | Accuracy (%) | 103.6 | 101.3 | 99.3 | 99.4 | |

TABLE 1-continued

Precision and accuracy of folate analyses (n = 15)

| Analyte | Parameter | LLOQ (nmol/L) | LQC (nmol/L) | MQC (nmol/L) | HQC (nmol/L) | UQC (nmol/L) |
|---|---|---|---|---|---|---|
| 5,10-MTHF | Mean | 4.2 | 10.3 | 41.2 | 167.4 | |
| | Precision (%) | 8.1 | 6.1 | 6.5 | 5.8 | |
| | Accuracy (%) | 96.9 | 94.7 | 94.1 | 95.5 | |

Abbreviations;
LLOQ, lower limit of quantitation;
LQC, lower quality control;
MQC, middle quality control;
UQC, upper quality control;
FA, folic acid;
5-MTHF, 5-methyltetrahydrofolate;
THF, tetrahydrofolate;
5,10-MTHF, 5,10-methenyltetrahydrofolate.

TABLE 2

Replicate analyses (n = 5) with different RBC samples (n = 5)

| Subject | FA (nmol/L) | CV | 5-MTHF (nmol/L) | CV | THF (nmol/L) | CV | 5,10-MTHF (nmol/L) | CV |
|---|---|---|---|---|---|---|---|---|
| A | ND | ND | 826.7 | 6.5% | 20.5 | 12.5% | ND | ND |
| B | ND | ND | 715.2 | 4.5% | 21.9 | 12.5% | ND | ND |
| C | ND | ND | 812.3 | 5.1% | 24.2 | 9.8% | ND | ND |
| D | ND | ND | 1269.4 | 3.9% | 60.9 | 7.4% | 17.5 | 7.1% |
| E | ND | ND | 738.4 | 2.0% | 32.0 | 14.9% | ND | ND |
| Mean | ND | ND | 826.7 | 4.4% | 31.9 | 11.4% | 3.5 | 7.8% |

Abbreviations:
ND, not detected;
other abbreviations as for Table 1.

Analysis of RBC Folates

Mature RBCs are unable to accumulate or export folate derivatives (Lamers et al., 2006, Am. J. Olin. Nutr. 84(1):156-61; Bailey, 1990, J. Nutr. 120(Suppl 11):1508-11), and the current folate content of each RBC reflects that present at the time of its formation through erythropoiesis (Bagley et al., 1998, Proc. Natl. Acad. Sci. USA 95(22):13217-20). As the life span of a normal RBC is approximately 120 days, RBC folate measurements reflect the average levels during the preceding 4 months, in contrast to plasma or serum folate levels which exhibit transient fluctuations due in part to daily differences in dietary intake (Herbert, 1987, Am. J. Hematol. 26(2):199-207). Therefore, RBC folate content has been used as a surrogate biomarker for historical folate status over the medium term. The present study was designed to develop a methodology that could distinguish different phenotypes between and within the three MTHFR 677C>T genotype classes. Particularly because 5-FTHF was observed to be present in RBCs of individuals with the MTHFR 677TT genotype.

The present invention allows for further stratifying disease risk associated with disruptions to the folate pathway. Stable isotope dilution LC-MRM/MS affords an opportunity to define such phenotypes with high precision. The present methodology allows for the generation of distinct phenotypes inclusive of the key folate metabolites. It has been reported shown that a high-throughput method in which 5-MTHF, THF, 5,10-MTHF, and 5-FTHF were analyzed directly in 38 subjects with defined MTHFR 677C>T genotypes (Fazili et al., 2004, Clin. Chem. 50(12):2378-81). However, 10-FTHF was unstable under the assay conditions used. In contrast to the present study, no distinct RBC folate phenotypes were reported for the three different MTHFR 677C>T genotypes.

Furthermore, the present results show an unexpected high 5-FTHF concentration in MTHFR 677CC homozygotes compared with the previous study of Bagley and Selhub (Bagley et al., 1998, Proc. Natl. Acad. Sci. USA 95(22):13217-20).

Figure 5:
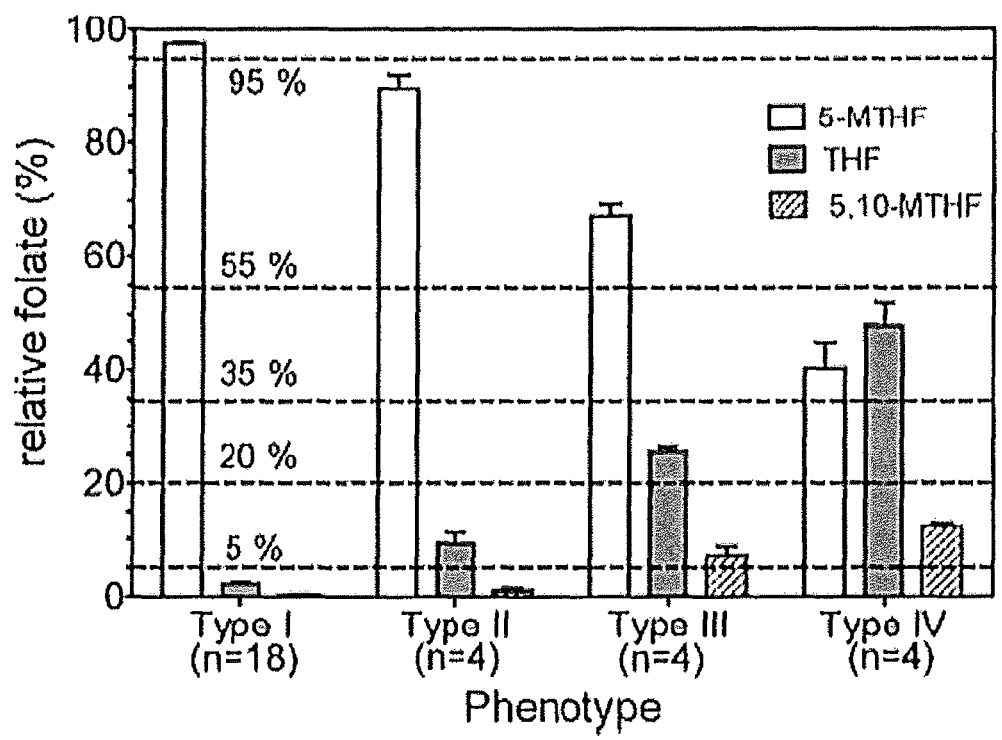
FIG. 5 is a chart depicting folate phenotypes based on the relative amounts of RBC folates: type I (5-MTHF>95%; THF<5%; 5,10-MTHF<5%) comprised ten TT, seven CT, and one TT genotype; type II 5-MTHF<95%; THF>5% to 20%; 5,10-MTHF<5%) comprised three CT and one TT genotype; type III (5-MTHF>55%; THF>20%; 5,10-MTHF>5%) comprised four TT genotypes; type IV (5-MTHF<55%; THF>20%; 5,10-MTHF>5%) comprised four TT genotypes.

The analysis of RBC folates provides a significant bioanalytical challenge because the individual forms of folates are retained in the RBCs after erythropoiesis by virtue of polyglutamylation in which varying numbers of glutamate residues are added to the folates. In order to rigorously quantify the individual folates, it is necessary to first hydrolyze the folylpolyglutamates to their corresponding monoglutamate forms (FIG. 1). Plasma enzymes that typically perform this function have optimal activities at acidic pH, under which conditions formylated folates are converted into 5,10-MTHF. Therefore, the experiments were designed to analyze the formylated folate derivatives as 5,10-MTHF after their acid-catalyzed conversion to the latter. This conversion was conducted in the presence of $[^{13}C_5]$-5-FTHF to ensure that no residual formylated folate derivatives remained by including the relevant MRM transitions in the LC/MS analyses. The resulting $[^{13}C_5]$-5,10-MTHF was then used as the internal standard to quantify all of the unlabeled 5,10-MTHF that had been formed from 5-FTHF and 10-FTHF as well as any unlabeled 5,10-MTHF that had been present at the time of sample collection. Analyses of RBC folates from 30 genotyped individuals (ten MTHFR 677CC homozygotes, ten MTHFR 677CT heterozygotes, and ten MTHFR 677TT homozygotes) were conducted using the stable isotope dilution LC-MRM/MS methodology. It was observed that the dominant form of folate in most samples was 5-MTHF (Table 3). However, there were distinct differences in folate distribution patterns between and within the MTHFR 677C>T genotype classes. Generally, RBCs from both MTHFR 677 CC homozygotes and CT heterozygotes had very low levels of THF (i.e. <5% total folate) and almost undetectable amounts of 5,10-MTHF (FIG. 3; Table 3). However, THF, but not 5,10-MTHF, could be detected at a higher level (i.e. >5% total folate) in three of the CT heterozygotes. This resulted in a higher mean THF value of 42.0 nmol/L or 4.3% of total folates for the ten CT genotypes that were analyzed (Table 3). The above two folate distribution patterns suggested the existence of two distinct phenotypes, designated type I (5-MTHF>95%; THF<5%; 5,10-MTHF<5%) and type II (5-MTHF<95%; THF 5% to 20%; 5,10-MTHF<5%), respectively, within the two main genotype classes (FIG. 5). In contrast to the CC and CT genotypes, 5,10-MTHF was readily detectable (mean 8.0% of total folate) in RBCs from TT homozygotes (Table 3) indicating that the TT phenotypes are more complex than the CC and CT genotypes with respect to RBC folate distribution. Furthermore, RBCs from TT homozygotes had much higher amounts of THF (mean 30.2% of total folate) than RBCs from those with the CC and TT genotypes (Table 3). There appears to be at least two distinct TT phenotypes, defined by the relative amounts of 5-MTHF, THF, and 5,10-MTHF (FIG. 5). Accordingly, the two phenotypes within the MTHFR 677TT genotype class have been designated type III (5-MTHF>55%; THF>20%; 5,10-MTHF>5%) and type IV (5-MTHF<55%; THF>20%; 5,10-MTHF>5%), as shown in FIG. 5. Pending further investigation involving larger numbers of individuals, the type III and IV phenotypes can be collectively identified by THF and 5,10-MTHF levels that exceed 20% and 5% of total RBC folate, with further subdivision being defined by 5-MTHF concentrations above 55% or below 55% of total folates, respectively (FIG. 5). Intriguingly, one of the ten TT homozygotes had a type I phenotype and another had a type II phenotype. Thus, MTHFR 677TT genotype alone does not appear to be sufficient unequivocally to define the phenotype of a particular subject, suggesting that, for a minority of MTHFR 677TT homozygotes, additional biochemical and/or genetic variables are involved in determining the relative amounts of individual folate metabolites. The finding of increased THF and 5,10-MTHF concentrations in RBCs from MTHFR 677TT homozygotes is in keeping with the concept that the thermolabile enzyme variant defined by this genotype has impaired capacity for mediating the conversion of 5-METHF into 5-MTHF. Alternative biochemical pathways such as those involved in DNA synthesis can then be up-regulated, in utilizing the 5,10-METHF that is not converted into 5-MTHF, and thereby favoring the accumulation of THF and 5,10-MTHF. This can occur through increased thymidylate synthase-mediated thymidine phosphate biosynthesis (with concomitant formation of THF) as well as from 10-FTHF-mediated increases in purine biosynthesis, which result from conversion of 5,10-METHF into 10-FTHF by MTHFD, a trifunctional enzyme with both dehydrogenase and cyclohydrolase activity (Prasannan et al., 2003, J. Biol. Chem. 278(44):43178-87).

TABLE 3

Mean folate content of RBCs (n = 30) from three different MTHFR 677C > T genotypes

| Subject | 5-MTHF | | THF | | 5,10-MTHF | | Total |
|---|---|---|---|---|---|---|---|
| | nmol/L | % | nmol/L | % | nmol/L | % | nmol/L |
| CC mean (n = 10) | 929.6 | 97.7 | 21.3 | 2.0 | 4.0 | 0.4 | 955.0 |
| SD | 285.7 | — | 15.3 | — | 6.5 | — | — |
| CT mean (n = 10) | 1065.4 | 95.2 | 42.0 | 4.3 | 5.4 | 0.5 | 1112.8 |
| SD | 360.4 | — | 34.7 | — | 7.4 | — | — |
| TT mean (n = 10) | 764.0 | 61.8 | 374.5 | 30.2 | 100.4 | 8.0 | 1239.0 |
| SD | 292.3 | — | 249.4 | — | 73.5 | — | — |

Abbreviations:
CC, MTHFR 677CC genotype;
CT, MTHFR 677CT genotype;
MTHFR 677TT genotype;
other abbreviations as for Tables 1 and 2.

Quantification of Key Red Blood Cell Folates from Subjects with Defined MTHFR 677C>T Genotypes Using Stable Isotope Dilution Liquid Chromatography/Mass Spectrometry The analysis of RBC folates provides a surrogate biomarker for folate status of an individual because RBCs are unable to transport and accumulate folate derivatives (Herbert, 1987, Am. J. Hematol. 26(2):199-207). Therefore, they reflect the folate status of an individual at the time of erythropoiesis (Bagley et al., 1998, Proc. Natl. Acad. Sci. USA 95(22): 13217-20). Individual folates are present as folylpolyglutamates, which prevents their secretion from the RBCs. Therefore, it was first necessary to convert them into the corresponding monoglutamates prior to analysis. This was accomplished using an individual's own plasma pteroylpolyglutamate hydrolase by simply lysing the RBCs in a whole blood sample. Optimal polyglutamate hydrolysis occurs at pH 5 so the whole blood was treated with ascorbic acid in order to reduce the pH to this level (Quinlivan et al., 2006, Anal. Biochem. 348(2):163-84; Pfeiffer et al., 1996, Clin. Chem, 42(11):1847-54). The ascorbic acid also served as an antioxidant to prevent loss of the labile THF derivatives. Unfortunately, under these conditions, substantial amounts of the formylated THFs were dehydrated to 5,10-MTHF. Therefore, the dehydrations were allowed to go to completion at pH 1.5 in the presence of $[^{13}C_5]$-5-FTHF, which was also converted into $[^{13}C_5]$-5,10-MTHF. The resulting $[^{13}C_5]$-5,10-MTHF was then used as an internal standard for the formylated forms of THF that had been converted into 5,10-MTHF as well as the 5,10-MTHF that was present in the original sample (FIG. 1). A stable isotope dilution LC-MRM/MS method was developed for the accurate and precise quantification of the spectrum of the resulting RBC folates.

The method was sensitive and robust, and was used to assess the relationship between different MTHFR 677C>T genotypes and RBC folates in 30 genotyped subjects. This indicated that there are four different phenotypes that are differentially distributed between the MTHFR 677C>T genotype classes (FIG. 5). The assay is can be used in combination with analyses of homocysteine and glutathione for extensive phenotyping studies in human populations with defined genotypes. The methodology described herein has the potential to identify subgroups of individuals with genotype/phenotype profiles that confer excess risk of pathologies that are known to be associated with dysfunction in folate/homocysteine metabolism. Such genotype/phenotype-based risk estimation may be used in the conduct of clinical studies and to develop predictive and diagnostic screening protocols.

Example 2

Genetic and Biochemical Determinants of Serum Concentrations of Monocyte Chemoattractant Protein-1, a Potential Neural Tube Defect Risk Factor Women with the AA genotype at the (–2518) A>G promoter polymorphism of CCL-2, which encodes monocyte chemoattractant protein 1 (MCP-1), is believed to be at increased risk for having offspring affected by spina bifida. As the A allele at this locus has been associated with decreased transcription of MCP-1 mRNA relative to the G allele, the observed genetic association suggests that the risk of spina bifida may be increased in the offspring of women with low MCP-1 levels.

The present study was undertaken to identify potential determinants of MCP-1 levels in women of reproductive age. A small cohort of Caucasian and African-American women of reproductive age was recruited to participate in an investigation of the determinants of several disease-related, biochemical phenotypes, including MCP-1. Subjects completed a brief questionnaire and provided a fasting blood sample for biochemical and genetic studies. Potential biochemical, genetic and lifestyle factors were assessed for their association with MCP-1 levels using linear regression analyses.

The results presented herein demonstrate that in this cohort, MCP-1 levels were significantly higher in Caucasians as compared to African-Americans. Further, among women of both races, there was evidence that MCP-1 levels were associated with smoking status, MTHFR 677C>T genotype and red blood cell tetrahydrofolate levels. Without wishing to be bound by any particular theory, it is believed that any relationship between CCL-2, MCP-1, and spina bifida risk may depend upon folate intake, MTHFR 677C>T genotype, the distribution of folate derivatives, and immune/inflammatory activity.

The materials and methods employed in the experiments disclosed herein are now described.

Study Subjects

Pre-menopausal female subjects were recruited from staff and students at the University of Pennsylvania School of Medicine. Potential study subjects were excluded if they had a major medical condition (e.g. autoimmune disease), were using an anti-folate medication, or were pregnant. The study was approved by the Institutional Review Board of the University of Pennsylvania School of Medicine, and all subjects provided informed consent.

The analyses presented herein are based on values obtained at the first visit, during which subjects provided a fasting blood sample and completed a short, in-person interview that included questions related to use of alcohol, smoking status, height and weight.

Laboratory Methods

Serum MCP-1 levels were measured using a human MCP-1 ELISA kit (BD Biosciences) according to the manufacturer's instructions. Total homocysteine (tHcy) and both plasma and red blood cell (RBC) folate derivatives were measured using stable isotope dilution liquid chromatography, multiple reaction monitoring, mass spectrometry (LC/MRM/MS) as described elsewhere herein. The measured folate derivatives were 5-MTHF, THF, and 5,10-MTHF.

Levels of C-reactive protein were measured in the clinical laboratory of the Hospital of the University of Pennsylvania using VITROS MicroSlides (Ortho-Clinical Diagnostics).

Genotyping

DNA was extracted from whole blood using the QIAamp@ DNA Mini Kit (Qiagen). MTHFR 677C>T, MTHFR 1298 A>C and CCL-2 (-2518) A>G allelic discrimination was performed using TaqMan 5' Nuclease Real-Time PCR assays on a DNA Engine Opticon 2 Continuous Fluorescence Detection System (MJ Research, Waltham, Mass.). Probes were custom synthesized by Applied Biosystems. In each case, dual fluorescence was detected after each extension 5' nuclease step, and genotype interpretations were performed using OpticonMonitor Analysis software version 2.02 (MJ Research).

For MTHFR 677C>T genotyping, PCR amplifications were performed as described elsewhere herein. Briefly, 4-25 ng of sample DNA, 0.5 µM each of forward (5'-GCAGG-GAGCTTTGAGGCTGACC-3'; SEQ ID NO: 1) and reverse (5'-TGGGGCAAGTGATGCCCATGT-3'; SEQ ID NO: 2) primers, together with 50 nM "T"-allele probe (5'-6FAM-ATGAAATCGACTCCCGC-3'-MGBNFQ; SEQ ID NO: 3) and 100 nM "C"-allele probe (5'-VIC-ATGAAATCGGCTC-CCGC-3'-MGBNFQ; SEQ ID NO: 4) were combined in 20 µl 1× Taqman Universal PCR MasterMix (Applied Biosystems, Foster City, Calif.). PCR was performed with an initial incubation at 95° C. for 10 min, followed by 60 cycles of denaturation at 95° C. for 30 sec and extension/5' nuclease step at 56° C. for 1 min.

For MTHFR 1298A>C genotyping, PCR amplifications were performed as described elsewhere herein. Briefly, 4-25 ng of sample DNA, 0.5 µM each of forward (5'-GAGGAGCT-GCTGAAGATGT-3'; SEQ ID NO: 5) and reverse (5'-CGAGAGGTAAAGAACGAAGA-3'; SEQ ID NO: 6) primers, together with 50 nM each of "T"-allele probe (5'-6FAM-AGACACTTGCTTCACT-3'-MGBNFQ; SEQ ID NO: 7) and "C"-allele probe (5'-VIC-CAAAGACACTTTCTTC-3'-MGBNFQ; SEQ ID NO: 8) were combined in 20 µl 1× Taqman Universal PCR MasterMix (Applied Biosystems). PCR was performed with an initial incubation at 92° C. for 10 min, followed by 60 cycles of denaturation at 92° C. for 1 min and extension/5' nuclease step at 60° C. for 1 min.

For CCL-2 (-2518) A>G genotyping, PCR amplifications were performed as described previously (Jensen et al., 2006, Am J Med Genet A 140(10):1114-1118) with minor modification. Briefly, 4-25 ng genomic DNA, 0.5 µM each of forward (5'-TTCTTGACAGAGCAGAAGTGG-3'; SEQ ID NO: 9) and reverse (5'-GCCTTTGCATATATCAGACAGTA-3'; SEQ ID NO: 10) primers, together with 50 nM each of "A"-allele probe (5'-6FAM-AGACAGCTATCACTT-3'-MGBNFQ; SEQ ID NO: 11) and "G"-allele probe (5'-VIC-AGA-CAGCTGTCACTTTC-3'-MGBNFQ; SEQ ID NO: 12) were combined in 20 µl Taqman master mix (Applied Biosystems). PCR was performed with an initial incubation at 95° C. for 10 min, followed by 60 cycles of denaturation at 95° C. for 15 seconds and extension/5' nuclease step at 57° C. for 30 seconds.

Statistical Methods

Descriptive analyses of the study variables included counts and proportions for discrete variables, and means and standard deviations for continuous variables. Body mass index (BMI) was calculated as: weight(kg)/[height(m)]$^2$, and total RBC folate as the sum of RBC 5-MTHF, THF and 5,10-MTHF. Simple linear regression analyses were performed with MCP-1 levels as the outcome measure. The coefficient of determination ($R^2$) estimated from these models was used to assess the proportion of variation in MCP-1 levels that was explained by each predictor variable. The significance of the association between each predictor variable and MCP-1 levels was assessed using the t-statistic. All analyses were performed separately by race, using data obtained during the first study visit and SAS version 9.1 (SAS Institute, Inc, Cary, N.C.). Values of $R^2 \geq 0.10$ and p-values<0.10 were considered of interest.

The results are now described. A total of 53 women consented to participate in this study. However, four (7%) were subsequently found to have medical conditions and/or to be taking medications that fell within the study exclusion criteria. The data from these four women were excluded from all analyses. Among the remaining 49 women, mean age was 32.5 years (range: 22.2-49.1 years) at the first study visit, and self-repotted race was Caucasian in 26 (53%) and African American in 23 (47%).

The characteristics of the study subjects at the time of the first study visit are summarized, separately by race, in Table 4, As MCP-1 levels were significantly lower in African American as compared to Caucasian subjects (t=2.46, p=0.02 from simple linear regression of race on MCP-1), and several of the potential predictor variables were also distributed quite differently in African Americans and Caucasians (Table 4), all analyses were performed separately by race.

TABLE 4

Subject characteristics, biochemical phenotypes and genotypes (mean ± s.d. or count and percentage).

| Variable | Race African-Americans (N = 23) | Caucasians (N = 26) |
|---|---|---|
| Subject Characteristics | | |
| Age (years) | 31.6 ± 6.0 | 33.3 ± 6.5 |
| Body mass index (kg/m$^2$) | 28.3 ± 5.9 | 23.5 ± 3.4 |
| Cigarettes | | |
| Yes | 4 (17.4) | 5 (19.2) |
| No | 19 (82.7) | 21 (80.8) |
| Alcohol intake | | |
| Yes | 16 (69.6) | 22 (84.6) |
| No | 7 (30.4) | 4 (15.4) |
| Biochemical Phenotypes | | |
| MCP-1 (pg/mL) | 164.4 ± 110.3 | 244.4 ± 116.3 |
| Homocysteine (μmol/L) | 8.9 ± 2.5 | 9.6 ± 2.7 |
| RBC folate (μmol/L)[1] | 937.5 ± 341.0 | 1185.5 ± 329.1 |
| RBC 5-MTHF (nmol/L) | 919.3 ± 334.1 | 1040.3 ± 333.0 |
| RBC THF (nmol/L) | 17.5 ± 11.1 | 117.8 ± 214.5 |

TABLE 4-continued

Subject characteristics, biochemical phenotypes and genotypes (mean ± s.d. or count and percentage).

| Variable | Race African-Americans (N = 23) | Caucasians (N = 26) |
|---|---|---|
| RBC 5,10-MTHF | | |
| 0 nmol/L | 21 (91.3) | 10 (38.5) |
| >0 nmol/L | 2 (8.7) | 16 (61.5) |
| RBC THF:5-MTHF | 0.02 ± 0.01 | 0.2 ± 0.5 |
| Plasma 5-MTHF (nmol/L) | 33.5 ± 17.2 | 48.4 ± 20.5 |
| C-reactive protein | | |
| ≤0.9 mg/dL | 4 (17.4) | 2 (7.7) |
| >0.9 mg/dL | 19 (82.6) | 24 (92.3) |
| Genotypes | | |
| CCL-2 (−2158)A > G | | |
| AA | 16 (69.6) | 13 (50.0) |
| AG | 7 (30.4) | 10 (38.5) |
| GG | 0 (0.0) | 3 (11.5) |
| MTHFR 677C > T | | |
| CC | 16 (69.6) | 8 (30.8) |
| CT | 7 (30.4) | 13 (50.0) |
| TT | 0 (0.0) | 5 (19.2) |
| MTHFR 1298A > C | | |
| AA | 13 (56.5) | 14 (53.8) |
| AC | 10 (43.5) | 10 (38.5) |
| CC | 0 (0.0) | 2 (7.7) |

[1]RBC folate = (RBC 5-MTH) + (RBC THF) + (RBC 5,10-MT)

Subject Characteristics

MCP-1 concentrations were not associated with age or BMT in either African-American or Caucasian study subjects (Table 5). However, MCP-1 levels were associated with current smoking status ($R^2=0.13$); MCP-1 concentrations were higher among smokers in both races (Tables 5 and 6). In Caucasians, but not African-Americans, alcohol use also was associated with MCP-1 levels. However, this association is likely to reflect an inverse association between smoking status and alcohol use (i.e. smokers reported less alcohol use than non-smokers in both racial groups) that was stronger in the Caucasian (odd ratio (OR)=0.03, 95% confidence interval (CI) 0.002-0.49) than in the African-American (OR=0.36, 95% CI 0.04-3.26) subjects.

TABLE 5

Proportion of variation ($R^2$) in MCP-1 levels explained by selected subject characteristics, biochemical phenotypes and genotypes, by race.

| Variables | Race African-American (N = 23) | | Caucasian (N = 26) | |
|---|---|---|---|---|
| | Variable Coefficient (SE) | $R^2$ (P-value) | Variable Coefficient (SE) | $R^2$ (P-value) |
| Subject Characteristics | | | | |
| Age (years) | −1.0 (4.0) | 0.003 (0.80) | 2.7 (3.6) | 0.02 (0.46) |
| Body mass index (kg/m$^2$) | 3.7 (4.0) | 0.04 (0.36) | −5.3 (6.8) | 0.02 (0.45) |
| Cigarettes (yes/no) | 102.6 (58.0) | 0.13 (0.09) | 103.2 (55.2) | 0.13 (0.07) |
| Alcohol (yes/no) | −31.8 (50.7) | 0.02 (0.54) | −118.7 (59.8) | 0.14 (0.06) |
| Biochemical Phenotypes | | | | |
| Homocysteine (μmol/L) | −3.4 (9.7) | 0.01 (0.73) | 4.2 (8.9) | 0.01 (0.64) |
| RBC folate (nmol/L)[1] | −0.06 (0.07) | 0.04 (0.38) | 0.04 (0.07) | 0.02 (0.54) |

TABLE 5-continued

Proportion of variation ($R^2$) in MCP-1 levels explained by selected subject characteristics, biochemical phenotypes and genotypes, by race.

| | Race | | | |
|---|---|---|---|---|
| | African-American (N = 23) | | Caucasian (N = 26) | |
| Variables | Variable Coefficient (SE) | $R^2$ (P-value) | Variable Coefficient (SE) | $R^2$ (P-value) |
| RBC 5-MTHF (nmol/L) | −0.06 (0.07) | 0.03 (0.41) | −0.05 (0.07) | 0.02 (0.52) |
| RBC THF (nmol/L) | −3.8 (2.0) | 0.15 (0.07) | 0.2 (0.1) | 0.11 (0.10) |
| RBC 5,10-MTHF[2] | −61.7 (82.5) | 0.03 (0.46) | 8.0 (47.8) | 0.00 (0.87) |
| RBC THF: RBC 5-MTHF | −4637.7 (1914.2) | 0.22 (0.02) | 86.3 (44.7) | 0.13 (0.07) |
| Plasma 5-MTHF (nmol/L) | −1.3 (1.4) | 0.04 (0.35) | −0.9 (1.1) | 0.03 (0.44) |
| C reactive protein (mg/dL)[3] | −37.0 (61.6) | 0.02 (0.55) | 118.6 (83.9) | 0.08 (0.17) |
| Genotypes | | | | |
| CCL-2 (−2518)A > G[4] | | | | |
| AG | 10.1 (51.1) | 0.002 (0.85) | −28.8 (50.4) | 0.02 (0.77) |
| GG | — | | 19.8 (76.8) | |
| MTHFR 677C > T[4] | | | | |
| CT | 76.1 (48.4) | 0.11 (0.13) | −7.8 (49.1) | 0.19 (0.09) |
| TT | — | | 119.8 (62.3) | |
| MTHFR 1298A > C[4] | | | | |
| AC | −29.5 (47.1) | 0.02 (0.54) | −91.6 (46.0) | 0.16 (0.13) |
| CC | | | −92.1 (84.0) | |

[1] RBC folate = (RBC 5-MTH) + (RBC THF) + (RBC 5,10-MT)
[2] 0 nmol/L versus >0 nmol/L
[3] <9 mg/L versus >9 mg/L
[4] The rarer homozygous genotype was not observed among African-American subjects

TABLE 6

Mean MCP-1 level by race and other covariates

| | Mean MCP-1 Level, pg/mL (N) | |
|---|---|---|
| Variables | African-Americans | Caucasians |
| Total | 164.4 (23) | 244.4 (26) |
| Cigarettes | | |
| Yes | 249.2 (4) | 327.7 (5) |
| No | 146.6 (19) | 224.6 (21) |
| RBC THF[1] | | |
| ≤50$^{th}$ percentile | 175.6 (12) | 215.3 (13) |
| >50$^{th}$ percentile | 152.2 (11) | 273.5 (13) |
| RBC 5-MTHF[1] | | |
| ≤50$^{th}$ percentile | 172.6 (12) | 249.0 (13) |
| >50$^{th}$ percentile | 155.5 (11) | 239.8 (13) |
| MTHFR 677C > T | | |
| CC | 141.3 (16) | 225.3 (8) |
| CT | 217.3 (7) | 217.4 (13) |
| TT | — | 345.1 (5) |

[1] Race specific percentiles

Biochemical Phenotypes

It was observed that MCP-1 concentrations were not associated with tHcy, RBC folate, RBC 5-MTHF, RBC 5,10-MTHF, plasma 5-MTHF or C-reactive protein (Table 5). Among African-American women, MCP-1 levels were inversely associated with RBC THF ($R^2$=0.15) and the ratio of RBC THF to RBC 5-MTHF ($R^2$=0.22). In Caucasian women, MCP-1 levels were associated with RBC THF ($R^2$=0.11) and the ratio of RBC THF to RBC 5-MTHF ($R^2$=0.13), and the direction of these associations was the opposite of that observed in the African-American subjects.

Genotypes

It was observed that MCP-1 levels were not associated with CCL-2 (−2518) A>G genotypes, but were associated with MTHFR 677C>T genotypes in both African-American and Caucasian subjects (Tables 5 and 6). In both races, the MTHFR 677T allele was associated with increased MCP-1 levels. In African-Americans this allele appeared to have a dominant or co-dominant effect on MCP-1 levels (i.e. MCP-1 levels were increased in women with the CT as compared to CC genotype; there were no African-American women with the TT genotype in the study population). In Caucasians, the effect of the MTHFR 677T allele on MCP-1 levels appeared to be recessive (i.e. compared to women with the CC genotype, MCP-1 levels in women with the TT, but not the CT genotype, were increased). Although the effect of the MTHFR 677T allele appears to differ by race, it is possible that there is a dose response relationship between this allele and MCP-1 levels in both races, but that this relationship is obscured by relatively small numbers in each genotype category and the absence of the MTHFR 677TT genotype in the African-American subjects.

Among Caucasians, the MTHFR 1298A>C genotype was also associated with MCP-1 levels. However, since a similar association was not observed in African-Americans, this may be attributable to linkage disequilibrium between the two MTHFR variants.

Genetic and Biochemical Determinants

In the cohort of premenopausal women, MCP-1 levels were significantly lower in African-Americans as compared to Caucasians. Lower levels of MCP-1 in African-Americans relative to Caucasians have been previously reported (Bielinski et al., 2007, Genes Immun 8(8):684-690). In both races, the strongest predictors of MCP-1 levels appeared to be current smoking status, MTHFR 677C>T genotype and RBC THF levels. An association between MCP-1 levels and smoking status has also been previously reported (Bielinski et al., 2007, Genes Immun 8(8):684-690; McDermott et al., 2005, Circulation 112(8):1113-1120). However, the results presented herein are the first to indicate that MCP-1 levels are associated with either MTHFR genotype or RBC THF levels. However, in an experimental model of chronic mild folate depletion in endothelial cells, MCP-1 mRNA and protein synthesis were up-regulated (Brown et al., 2006, Atherosclerosis 189(1):133-141). Without wishing to be bound by any particular theory, it is believed that the observed association of MCP-1 levels with MTHFR 677C>T and RBC THF supports the hypothesis that perturbations in folate/homocysteine metabolism contribute to the induction of MCP-1 expression.

Given the relatively small samples sizes available in this study, it was not possible to accurately evaluate whether the observed association between MCP-1 levels and MTHFR 677C>T genotype or between MCP-1 levels and RBC THF levels were independent of each other. In addition, it was not possible to investigate the source of the difference in the observed association between RBC THF and MCP-1 levels in the African-American and Caucasian subjects. This difference may, however, be related to differences in the MTHFR 677C>T genotype distribution between Caucasians and African-Americans.

There was no evidence that MCP-1 levels in the tested subjects were associated with the CCL-2 (-2518) A>G polymorphism. The lack of such an association is believed to be associated with the presumptive absence of overt inflammatory stimuli in these study subjects. Indeed there is evidence from cell culture studies that pro-inflammatory stimuli, such as TNF-α, induce CCL-2 transcription via NF-κB, whereas folate insufficiency (under non-inflammatory conditions) induces CCL-2 transcription via a p38 dependent mechanism. The two pathways appear to be distinct, but have multiplicative effects when both are engaged The CCL-2 (-2518) G allele confers a cytokine dependent transcriptional advantage (Rovin et al., 1999, Biochem Biophys Res Commun 259(2):344-348) and hence this variant is believed to be associated with elevated MCP-1 levels in vivo only in the presence of inflammation. It is therefore likely that MCP-1 levels in the healthy subjects are being determined by the folate-dependent p38-mediated pathway, which does not appear to be influenced by the CCL-2 promoter polymorphism.

Several additional variables that have been reported to be significantly related to MCP-1 levels (e.g. age, BMX) were not identified as significant predictors of MCP-1 levels in this cohort. Given the small sample sizes in the present study, it is possible that some associations have been missed due to low study power. However, it is also possible that differences in findings between these and other studies reflect differences in the characteristics across study populations. The present study was based on healthy, reproductive age females, whereas many of the other published studies of the determinants of MCP-1 levels have focused on cohorts with a specific disease phenotype (e.g. cardiovascular disease, systemic lupus erythematosus), and included a broader age range, an older cohort, and/or both sexes (Bielinski et al., 2007, Genes Immun 8(8):684-690; Brown et al., 2007, J Rheumatol 34(4): 740-746; McDermott et al., 2005, Circulation 112(8):1113-1120).

It has been observed that women with the CCL-2 (-2518) AA genotype are at increased risk for having offspring affected with spina bifida. As the CCL-2 AA allele has been associated with decreased transcription and lower circulating levels of MCP-1, it is believed that low MCP-1 levels might also be associated with the risk of spina bifida, due to a less than optimal systemic and/or local response to infection early in the first trimester of pregnancy (Jensen et al., 2006, Am J Med Genet A 140(10):1114-1118). The experiments conducted investigated the relationship between several established (i.e. race, folate status) or strongly suspected (i.e. MTHFR 677C>T genotype) NTD risk factors and MCP-1 levels. It was observed that MCP-1 levels were higher in the subgroup of women who are at higher risk of having NTD affected offspring based on race (i.e. Caucasians) and MTHFR 677C>T genotype (i.e. MTHFR 677TT). It is believed that the results indicate that any effect of MCP-1 levels on the risk of NTDs, as suggested by the association between maternal CCL-2 (−2518)A>G genotype and NTD risk, is independent of these other risk factors. However, it is also believed that any relationship between this genotype, MCP-1 levels and NTD risk may also depend upon folate intake, genetically mediated distribution of folate derivatives, and immune/inflammatory activity. Such complexity seems likely given the separate folate-dependent and inflammation-dependent mechanisms that control MCP-1 expression.

Example 3

Folate and Homocysteine Phenotypes: Comparative Findings Using Research and Clinical Laboratory Data A low folate/high homocysteine phenotype is associated with several pathologies, including spina bifida and cardiovascular disease. Folate and total homocysteine (tHcy) measurements are used clinically to assess risk and the need for folic acid supplementation and in research to investigate the metabolic basis of disease. Red blood cell (RBC) folate, the best known indicator of long-term folate status, is usually measured as "total" folate. However, different folate derivatives support distinct biochemical functions, suggesting a need to develop more precise methods. The experiments presented herein were designed to evaluate a method based on stable isotope dilution liquid chromatography-multiple reaction monitoring/mass spectrometry (LC-MRM/MS).

LC-MRM/MS was used to quantify the RBC folate derivatives 5-MTHF, THF, and 5,10-MTHF in pre-menopausal women. The concentrations of each folate derivative was assessed for utility in predicting tHcy levels, and compared to folate and tHcy measurements derived using routine clinical laboratory methods.

The results demonstrated that LC-MRM/MS was qualitatively and quantitatively superior to routine clinical laboratory methods for determining folate and tHcy concentrations. RBC 5-$CH_3$-THF had a reciprocal relationship with tHcy (p-0.0003), whereas RBC THF and RBC 5,10-methenylTHF had direct relationships (p=0.01, 0.04 respectively). In combination, these three variables accounted for 42% of the variation in tHcy.

It is believed that robust methods for measuring RBC 5-$CH_3$-THF would improve the utility of folate/homocysteine phenotyping in patient management. The use of LC-MRM/MS would allow studies of hyperhomocysteinemia and diseases associated with a low folate/high homocysteine phenotype to be performed with less measurement error and greater statistical power to generate data with the potential to elucidate the etiologic mechanisms of complex diseases and traits.

The materials and method employed in the experiments disclosed herein are now described.

Study Subjects

Pre-menopausal Caucasian and African American female subjects were recruited through advertisements from staff and students at the University of Pennsylvania School of Medicine. Exclusionary criteria were major medical conditions, especially autoimmune disease, use of anti-folate medications, and pregnancy. All subjects gave written informed consent. Subjects attended two study visits, approximately four weeks apart, at each of which a short questionnaire was administered and blood drawn. The study was approved by the Institutional Review Board of the University of Pennsylvania School of Medicine.

Laboratory Methods

Blood was drawn for two parallel sets of analyses. Separate aliquots from the same draw were directed to the clinical and research laboratories:

Clinical Laboratory: Routine measurements of biochemical variables of interest were carried out using standard assays by a hospital clinical laboratory. Specifically, assays used were AxSYM Homocysteine (Abbott Diagnostics) for total homocysteine (tHcy), Immulite 2500 Folk Acid (Siemens Medical Solutions Diagnostics) for serum folate, and Advia Centaur Folate (Siemens Medical Solutions Diagnostics) for RBC total folate. Complete blood count (CBC) determinations, including hematocrit, were performed using a Beckman-Coulter LH785/780 instrument.

Clinical laboratory values are as reported by the facility. tHcy concentrations are expressed as µmol/L. RBC total folate concentrations are expressed in ng/mL, rather than nmol/L, as the analytical method used does not distinguish between the different constituent folate derivatives, for which the molecular masses differ slightly.

Research Laboratory: Stable isotope dilution LC-MRM/MS was used as previously described to measure tHcy (Huang et al., 2007 Biomed Chromatogr 21:107-12), and plasma and RBC folate derivatives as described elsewhere herein. Blood for RBC folate measurements was lysed in 1% ascorbic acid at pH5 prior to analysis of 5-$CH_3$-THF and THF, and prior to acidification to pH1.5 with HCl for analysis of 5,10-methenylTHF as described elsewhere herein.

Similar to the clinical laboratory, the research laboratory values for tHcy concentrations are expressed as µmol/L. In contrast to the clinical laboratory, the research laboratory reported concentrations for each of three folate derivatives (5-$CH_3$-THF, THF, and 5,10-methenylTHF), as well as for RBC total folate as the sum of the three derivatives, in nmol/L.

Statistical Methods

Descriptive analyses were undertaken to characterize the subjects enrolled in the study. Continuous variables were summarized using means, standard deviations, medians and ranges, and discrete variables were summarized using counts and proportions. Serum folate values, as measured by the clinical laboratory, were dichotomized (≦15 ng/mL versus>15 ng/mL) because this laboratory reported all values above 15 ng/mL as >15 ng/mL. The research laboratory measures of RBC 5,10-methenylTHF and plasma THF were considered as both continuous and discrete (not detectable versus>0 nmol/L) variables because of the high proportion of non-detectable values for each (63.3% and 20.4%, respectively). Differences between measures of the same variable obtained at the first and second visits were summarized using the absolute difference and its standard error.

Agreement between the clinical and research laboratory measurements of tHcy, and relative bias were assessed as described by Bland and Altman (1986 Lancet i:307-10). In addition, the distributions of subjects across three clinically relevant subgroups defined by clinical or research laboratory tHcy values: >13 µmol/L indicating hyperhoinocysteinemia and the need to consider high dose folic acid therapy; 10-13 µmol/L indicating the need to retest; and <10 µmol/L indicating values in the desirable range, were compared. Because the clinical and research laboratories used different units of measurement for RBC folate, agreement between these two measures could not be directly assessed. Consequently, the mean of the absolute difference between the values obtained for RBC total folate at visits 1 and 2 was expressed as a proportion of the mean value at visit 1, and the resulting proportions were compared for the clinical and research laboratory measures.

The strength of the relationship between the clinical laboratory measures of serum and RBC total folate, and the research laboratory measures of plasma folate, RBC total folate, and RBC folate derivatives were assessed using the Pearson correlation coefficient. In addition, linear regression analyses were used to assess the strength of the relationship between tHcy and both serum/plasma and RBC total folate levels, as measured by the clinical and research laboratories, and the strength of the relationship between tHcy and levels of the three individual folate derivatives, as measured by the research laboratory. All statistical analyses were conducted using SAS version 9.13 (SAS Institute Inc., Cary, N.C.).

The results of the experiments disclosed herein are now described.

A total of 53 subjects were consented into the study; however, after recognition of exclusionary conditions and medication use, 49 subjects (age 22-49 years) were enrolled: 26 and 23 self-identified as Caucasian and African American respectively. The second study visits ranged from 24 to 39 days (mean 32.6 days) after the first visit.

The mean value of the absolute difference between the tHcy values obtained at Visit 1 and Visit 2 was small for both the clinical and research laboratory measures (Table 7), indicating that this aspect of phenotype is relatively stable over a period of approximately one month. However, the standard deviation of this mean was considerably larger for the clinical laboratory (SD=2.2) than for the research laboratory (SD=1.3), indicating that the research laboratory values provide a more precise measure of tHcy.

TABLE 7

Summary of the biochemical phenotypes observed at Visit 1 and Visit 2

| Variables | Mean ± SD (median, range) or N (%) | | Mean of Absolute Difference ± SD (%)[a] |
|---|---|---|---|
| | Visit 1 | Visit 2 | |
| Clinical Laboratory Phenotypes | | | |
| Homocysteine (µmol/L) | 11.1 ± 2.6 (11.3, 6.4-18.1) | 11.5 ± 3.3 (11.3, 6.6-23.8) | 2.3 ± 2.2 (20.8) |
| RBC total folate (ng/mL) | 639.8 ± 152.0 (639.0, 397.0-1032.0) | 695.8 ± 192.5 (677.5, 383.0-1224.0) | 122.9 ± 103.2 (19.2) |

TABLE 7-continued

Summary of the biochemical phenotypes observed at Visit 1 and Visit 2

| Variables | Mean ± SD (median, range) or N (%) | | Mean of Absolute Difference ± SD (%)[a] |
|---|---|---|---|
| | Visit 1 | Visit 2 | |
| Serum folate | | | |
| ≤15 ng/mL | 19 (38.8) | 20 (40.8) | — |
| >15 ng/mL | 30 (61.2) | 29 (59.2) | — |
| Research Laboratory Phenotypes | | | |
| Homocysteine (μmol/L) | 9.2 ± 2.6 (9.0, 4.5-16.9) | 9.0 ± 2.6 (8.7, 5.5-19.1) | 1.3 ± 1.2 (13.6) |
| RBC total folate (nmol/L)[b] | 1069.1 ± 354.0 (1063.4, 507.6-2077.7) | 1052.7 ± 356.7 (1088.5, 422.5-2190.6) | 106.3 ± 88.9 (10.0) |
| RBC 5-CH$_3$-THF (nmol/L) | 983.5 ± 335.6 (963.1, 202.3-1661.1) | 968.9 ± 326.2 (1016.1, 149.9-1636.2) | 103.5 ± 86.8 (10.5) |
| RBC THF (nmol/L) | 70.7 ± 163.1 (21.3, 0.0-889.9) | 68.9 ± 159.8 (21.0, 0-864.9) | 8.7 ± 14.8 (12.3) |
| RBC 5,10-methenylTHF (nmol/L) | 14.9 ± 45.3 (0.0, 0.0-224.7) | 14.9 ± 37.5 (0, 0-198.5) | 5.2 ± 12.7 (35.2) |
| RBC 5,10-methenylTHF | | | |
| ND[c] | 31 (63.3) | 25 (51.0) | — |
| >0 nmol/L | 18 (36.7) | 24 (49.0) | — |
| Plasma 5-CH$_3$-THF (nmol/L) | 41.4 ± 20.3 (39.4, 6.2-91.3) | 42.1 ± 19.2 (41.4, 8.0-81.2) | 10.7 ± 9.1 (25.8) |
| Plasma THF (nmol/L) | 0.7 ± 0.4 (0.7, 0.0-1.5) | 0.6 ± 0.5 (0.7, 0-1.5) | 0.3 ± 0.3 (44.3) |
| Plasma THF | | | |
| ND[c] | 10 (20.4) | 16 (32.7) | — |
| >0 nmol/L | 39 (79.6) | 33 (67.3) | — |

Figure 7:
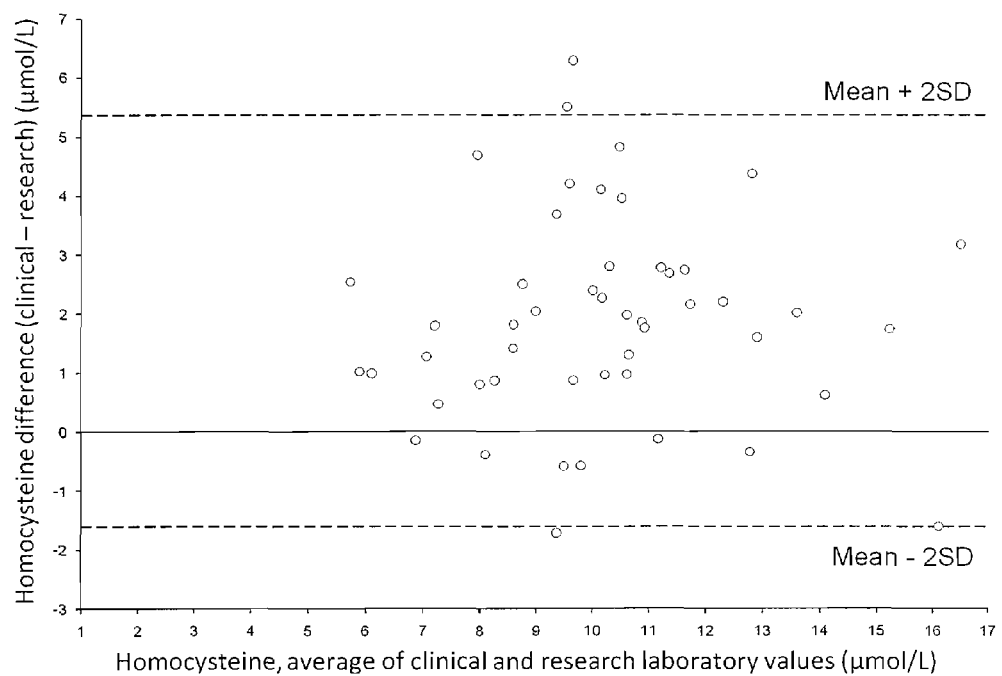
FIG. 7 is an image depicting the tHcy values measured using clinical and research laboratory methods. The difference between the clinical and research laboratory values was plotted against the mean of these two values for each subject.

[a]% = mean of absolute difference/Visit 1 mean
[b]RBC total folate = (RBC 5-CH$_3$-THF) + (RBC THF) + (RBC 5,10-methenylTHF)
[c]ND = non-detectable At both Visit 1 and Visit 2, mean tHcy concentrations obtained using the research laboratory method were approximately 20% lower than those reported using the clinical laboratory method (Visit 1: 9.2 vs 11.1; Visit 2: and 9.0 vs 11.5). To explore this disparity between the tHcy values measured using the clinical and research laboratory methods, the difference between the clinical and research laboratory values at Visit 1 was plotted against the mean of these two values for each subject (FIG. 7). FIG. 7 indicates that the values obtained using the clinical laboratory tend to be greater than those obtained for the same subject using the research laboratory (mean difference=1.88 μmol/L, standard deviation=1.74). The limits of agreement (mean difference±2 SD) indicate that the majority (~95%) of the clinical laboratory values fall between 1.60 μmol/L below and 5.4. μmol/L above the value obtained in the research laboratory. However, the maximum observed difference between the clinical and laboratory values of tHcy was 15.1 μmol/L.

Further comparison of the clinical and research laboratory tHcy measures, using clinically relevant cut-points (i.e. <10 μmol/L, 10-13 μmol/L, >13 μmol/L), indicated that the two laboratories provided the same classification for only 50% of the 98 study visits (i.e. 49 Visit 1 plus 49 Visit 2), and that there was an approximately two-fold difference in the number of visits at which subjects would be considered normal and require no follow-up or intervention (Table 8). Specifically, based on the clinical laboratory results (at Visit 1 or Visit 2) approximately 30% of subjects would be classified as being in the normal range (tHcy<10 μmol/L), whereas approximately 65% of subjects would be classified as such based on the research laboratory results.

TABLE 8

Comparison of homocysteine levels as measured by the clinical and research laboratories

| | Clinical Laboratory | | | | | | | |
|---|---|---|---|---|---|---|---|---|
| Research Lab | Visit 1 | | | | Visit 2 | | | |
| | <10 μmol/L | 10-13 μmol/L | >13 μmol/L | Total | <10 μmol/L | 10-13 μmol/L | >13 μmol/L | Total |
| <10 μmol/L | 13 | 18 | 0 | 31 (.63) | 15 | 14 | 5 | 34 (.69) |
| 10-13 μmol/L | 2 | 8 | 4 | 14 (.29) | 1 | 6 | 5 | 12 (.24) |
| >13 μmol/L | 0 | 0 | 4 | 4 (.08) | 0 | 0 | 3 | 3 (.06) |
| Total | 15 (.31) | 26 (.53) | 8 (.16) | 49 | 16 (.33) | 20 (.41) | 13 (.26) | 49 |

The mean values of the absolute difference between the RBC total folate values at Visit 1 and Visit 2 (Table 7), like those for tHcy, were relatively small for both the clinical and research laboratory methods. However, for the clinical laboratory method, the mean of the absolute difference was 19% of the visit 1 mean value, whereas for the research laboratory method, this proportion was only 10%, suggesting that the research laboratory method provides a more precise measurement of RBC total folate than does the clinical laboratory method.

The mean of the absolute difference between the research laboratory measurements of RBC 5-$CH_3$-THF at Visit 1 and Visit 2 was also relatively small (10% of the Visit 1 mean), indicating that RBC 5-$CH_3$-THF is relatively stable over a period of approximately one month. As expected, this difference was considerably larger for the research laboratory measurements of plasma RBC 5-$CH_3$-THF (26% of the Visit 1 mean). RBC THF also appeared to be relatively stable across this period (i.e. mean of absolute difference, 12% of Visit 1 mean). However, RBC 5,10-methenylTHF appeared to be more variable (i.e. mean of absolute difference, 35% of Visit 1 mean).

Serum folate levels, as determined by the clinical laboratory method, were significantly correlated (r=0.60) with the plasma 5-$CH_3$-THF levels obtained using the research laboratory method (Table 9). In addition, clinical laboratory measurements of RBC total folate levels were significantly correlated (r=0.73) with the research laboratory measurements of RBC total folate, as well as with each of the individual constituent folate derivatives (5-$CH_3$-THF, THF and 5,10-methenylTHF). Among the derivatives, clinical laboratory measurements of RBC total folate was most closely correlated with 5-$CH_3$-THF (r=0.55). However, it should be noted that all correlation coefficients were substantially below 1.0, indicating that RBC total folate measurements obtained using the clinical laboratory method provide relatively poor proxy measurements for the individual RBC folate derivatives.

TABLE 9

Correlations between serum and RBC folate measurements from the clinical laboratory and selected folate derivative measurements from the research laboratory.

| Clinical Laboratory | Research Laboratory | Correlation Coefficient (P-value) |
|---|---|---|
| Serum folate (ng/mL)[a] | Plasma 5-$CH_3$-THF (nmol/L) | 0.60 (<0.01) |
| Serum folate (ng/mL)[a] | Plasma THF (nmol/L) | 0.55 (<0.01) |
| RBC total folate (mg/mL) | RBC total folate (nmol/L)[b] | 0.73 (<0.01) |
| RBC folate (mg/mL) | RBC 5-$CH_3$-THF (nmol/L) | 0.55 (<0.01) |
| RBC folate (mg/mL) | RBC THF (nmol/L) | 0.36 (0.01) |
| RBC folate (mg/mL) | RBC 5,10 methenylTHF (nmol/L) | 0.38 (0.01) |

[a]Serum folate: ≦15 ng/mL versus >15 ng/mL
[b]RBC folate = (RBC 5-$CH_3$-THF) + (RBC THF) + (RBC 5,10-methenylTHF)

Linear regression analyses of the relationship between tHcy and the various folate measurements were undertaken separately in data from the clinical and research laboratories. Using data generated by the clinical laboratory, neither RBC total folate nor serum folate concentration was significantly related to tHcy concentration (Table 10), and the proportion of variation in tHcy levels accounted for by these variables was small (1% and 3%). In contrast, several of the RBC and plasma folate derivatives (measured by the research laboratory) were significantly related to the research laboratory's measurements of tHcy. Most notable is the highly significant (p=0.0003) inverse relationship between RBC 5-$CH_3$-THF and tHcy, the significant (p=0.01) direct relationship between RBC THF and tHcy, and the significant (p=0.04) direct relationship between RBC 5,10-methenylTHF and tHcy. Individually, these variables accounted for 25%, 13% and 9% of the variation in tHcy, respectively. It should be noted that the relationship between tHcy and RBC total folate, which is the sum of the above RBC folate derivatives, was of only borderline significance (p=0.07) and this measurement accounted for only 7% of the variation in tHcy. This is not unexpected as this composite measurement includes components that differ in the direction of their relationships with tHcy. Plasma 5-$CH_3$-THF was also significantly (p=0.02) and inversely related to tHcy, but this association, which accounted for 10% of tHcy variation, was not as strong as that with RBC 5-$CH_3$-THF. In contrast to RBC THF, plasma THF was inversely related to tHcy concentrations, but this association was of only borderline significance (p=0.08). When the research laboratory values of RBC 5-$CH_3$-THF, THF, and 5,10-methenylTHF were included in a regression model for tHcy, in combination they accounted for 42% of the variation in tHcy and each of these variables was significantly related to tHcy (p=0.0003, p=0.006 and p=0.002, respectively).

TABLE 10

Summary of linear regression analyses of homocysteine measurements from the clinical and research laboratories.

| Dependent variables | Predictors | Parameter estimate (SE) | $R^2$ (p-value) |
|---|---|---|---|
| Clinical Laboratory | | | |
| Homocysteine (µmol/L) | RBC total folate (ng/mL)[a] | −0.002 (0.002) | 0.01 (0.43) |
| Homocysteine (µmol/L) | Serum folate (ng/mL)[ba] | −0.84 (0.76) | 0.03 (0.28) |
| Research Laboratory | | | |
| Homocysteine (µmol/L) | RBC total folate (nmol/L)[b] | −0.002 (0.001) | 0.07 (0.07) |
| Homocysteine (µmol/L) | RBC 5-$CH_3$-THF (nmol/L) | −0.004 (0.001) | 0.25 (0.0003) |
| Homocysteine (µmol/L) | RBC THF (nmol/L) | 0.006 (0.002) | 0.13 (0.01) |
| Homocysteine (µmol/L) | RBC 5,10-methenylTHF (nmol/L) | 0.02 (0.01) | 0.09 (0.04) |
| Homocysteine (µmol/L) | Plasma 5-$CH_3$-THF (nmol/L) | −0.04 (0.02) | 0.10 (0.02) |
| Homocysteine (µmol/L) | Plasma THF (nmol/L) | −1.64 (0.93) | 0.06 (0.08) |

[a]RBC total folate = (RBC 5-$CH_3$-THF) + (RBC THF) + (RBC 5,10-methenylTHF)
[ab]Serum folate: ≦15 mg/mL versus >15 mg/mL
[b]RBC total folate = (RBC 5-$CH_3$-THF) + (RBC THF) + (RBC 5,10-methenylTHF)

Individuals with a low folate/high Hcy phenotype are considered to be at increased risk of several human pathologies (Lucock 2006 Curr Opin Clin Nutr Metab Care; 9:748-56). In particular, maternal low folate status before and very early in the first trimester of, pregnancy is a risk factor for spina bifida in offspring (Mitchell et al., 2004 Lancet 364:1885-95), and elevated tHcy is a risk marker for a range of atherothrombotic diseases (Refsum et al., 1998 Ann Rev Medicine 49:31-62). There is an inverse relationship between folate and tHcy concentrations (Harmon et al., 1996 Q J Med 1996 89:571-7; Stover, 2004 PJ. Physiology of folate and B12 in health and disease Nutr Res 62: 3-12, and several supplementation studies have shown that daily doses of as little as 200 μg folic acid or more effect a "normalizing" reduction in tHcy concentrations as well as a de facto improvement in folate status (Guttormsen et al., 1996 J Clin Invest 98:2174-83; Ward et al., 1997 QJM 90:519-24). In addition, diets that are rich in sources of natural folate, such as the Mediterranean diet, may be effective in lowering tHcy concentrations, particularly in those with a genetic predisposition to hyperhomocysteinemia (Dedoussis et al., 2004 Am J Clin Nutr 80: 849-54).

Patients with tHcy concentrations above 13 μmol/L are generally classified as having mild hyperhomocysteinemia, considered to be at elevated cardiovascular disease risk, and in many clinical practices would be prescribed a daily supplement containing 1 mg or more folic acid. A subsequent tHcy reading that remained above 13 μmol/L might trigger an increase in the amount of folic acid prescribed to 2 mg or even 5 mg per day. Commonly prescribed branded formulations are available in doses that reflect the above levels; for example, Folgard OS and Folgard RX tablets contain 1.1 mg folic acid and are often dispensed as a 30-day supply containing 60 tablets. Without wishing to be bound by any particular theory, it is believed that tHcy measurements between 10 μmol/L and 13 μmol/L might warrant retesting and in the event of a second test yielding a tHcy value above 13 μmol/L, the above decisions regarding the prescribing of folic acid supplements would come into play.

The disclosure presented herein suggest that tHcy measurements made by some clinical laboratories might be considerably different from those obtained using quantitatively precise LC-MRM/MS methods. The results demonstrate that the former exceeded the latter by approximately 2 μmol/L on average; however, there was considerable intra-individual variation in the absolute difference between the two analytic measurements, with single visit clinical laboratory values for some subjects being as much as 15.1 μmol/L higher than the research laboratory values. Consequently, some individuals with tHcy levels less than 10 μmol/L by LC-MRM/MS have clinical laboratory measurements above 13 μmol/L (5 of 98 assay pairs) or between 10 μmol/L and 13 μmol/L (32 of 98 assay pairs), which in a clinical setting might respectively trigger intervention with high dose folic acid by prescription or retesting. Furthermore, there were nine tHcy values at 10-13 μmol/L by LC-MRM/MS that were >13 μmol/L by clinical laboratory assay that might trigger folic acid prescription rather than retesting.

These findings result from a comparison of LC-MRM/MS measurements of tHcy with those obtained in a single clinical laboratory. These findings suggest that a substantial number of patients for whom tHcy measurements are routinely obtained might be inappropriately classified as hyperhomocysteinemic. Such misclassification could divert practitioners from a full clinical evaluation and treatment of other cardiovascular risk factors and might lead, in some individuals, to the generation of inaccurate cardiovascular risk profiles that could result in the initiation of unwarranted long-term remediation with high, or even very high, dose folk acid supplements. The issue of whether high dose folk acid supplements themselves constitute a health risk with respect to cancer has recently emerged. While a determination of the validity of such concerns over possible adverse consequences will require further large studies, it seems prudent to limit the number of individuals exposed to daily doses of folic acid that are between five and twenty-five times those (i.e. 200 μg per day) that are known to be sufficient to resolve mild hyperhomocysteinemia in the majority of the population, and that are multiples higher than the recommended dietary reference intake (Guttormsen et al., 1996 J Clin Invest 98:2174-83; Ward et al., 1997 QJM 90:519-24).

The disclosure presented herein suggests that LC-MRM/MS can be used in conjunction with the methods for measuring folates that are currently used by clinical laboratories to determine clinically relevant cut-points, thereby facilitating standard criteria for interventions using folic acid supplements.

RBC total folate levels are considered to be better indicators of long-term folate status, and to better reflect tissue levels, than serum/plasma folate concentrations, which are more transient. The data presented here indicate that the preferably specific measure for evaluating the reciprocal relationship between folate and tHcy concentrations is RBC 5-CH$_3$-THF. Indeed, RBC THF and 5,10-methenylTHF concentrations were both positively correlated with tHcy concentrations. This establishes the utility of developing robust methods appropriate for clinical laboratories that could be used to accurately assay RBC 5-CH$_3$-THF when folate status is being evaluated in the context of tHcy concentrations and other folate-dependent phenotypic variables.

The data presented herein support the use of cutting edge, quantitatively precise assays for measuring both folates and tHcy in human studies designed to explore the complex interrelationships between components of folate/Hcy metabolism per se, and in the context of hyperhomocysteinemia and pathologies in which a low folate/high Hcy phenotype has been causally implicated. It is believed that the precision of these assays will result in less measurement error and, hence, improved power relative to studies that employ quantitatively less precise assays. Without wishing to be bound by any particular theory, future studies in which folate and tHcy concentrations are an integral part, RBC 5-CH$_3$-THF (and possibly other folate derivatives) should be assessed, rather than RBC total folate, using quantitatively precise methods such as LC-MRM/MS. Such studies would permit more reliable conclusions to be drawn regarding folate/Hcy metabolism per se, and its contribution to disease etiology.

Example 4

Effects of MTX on Biochemical Parameters in Caucasians

The following experiments were designed to assess the phenotypic changes elicited by low dose methotrexate (MTX) treatment. MTX has been widely used as the anti-inflammatory and immunomodulatory agent for the treatment of patients with rheumatoid arthritis and other inflammatory disorders by weekly low-dose (7.5-25 mg).

The disclosure presented herein suggests that MCP-1 concentrations are associated with RBC THF concentrations and RBC THF:5-MTHF ratios. Furthermore, the data presented in Table 11 demonstrate that after treatment of arthritis patients with MTX, it was observed that RBC total folate and 5-MTHF levels fall (both p<0.0001) whereas RBC THF and 5,10-MTHF rise (p=0.0006 and p<0.0001 respectively). This indicates a quantitative and qualitative modification of folate phenotype (even though folic acid supplements were prescribed along with the MTX) that results in elevated MCP-1 concentrations (p<0.0001). These highly significant observations were made in only 115 subjects who exhibited clinical improvement, as evidenced by improved Physician Global Assessment (PGA, Table 11) and American Rheumatology Association (not shown) scores and lower CRP concentrations (Table 11).

TABLE 11

The effects of MTX on biochemical parameters in Caucasians

| Variable | No of samples (pairs) | Baseline (mean ± SD) | 24 wk (mean ± SD) | P-value Wilcoxon (signed rank test) |
|---|---|---|---|---|
| MCP1 | 128 | 370.9 ± 215.4 | 422.4 ± 231.1 | <0.0001 |
| RBCfolate | 115 | 1379.5 ± 584.1 | 1227.8 ± 532.7 | 0.0001 |
| RBC5MTH | 115 | 1276.7 ± 579.1 | 1115.2 ± 519.8 | <0.0001 |
| RBCTHF | 115 | 84.0 ± 175.2 | 88.8 ± 166.4 | 0.0006 |
| RBC5,10MT | 115 | 18.7 ± 45.9 | 23.8 ± 51.7 | <0.0001 |
| RBC(THF/5MTH) | 115 | 0.118 ± 0.387 | 0.175 ± 0.757 | <0.0001 |
| RBC (5,10MT/5MTH) | 115 | 0.026 ± 0.095 | 0.051 ± 0.241 | <0.0001 |
| Plasma 5MTH | 119 | 53.14 ± 31.14 | 39.90 ± 31.51 | <0.0001 |
| Plasma FA | 119 | 7.10 ± 26.62 | 36.20 ± 63.60 | <0.0001 |
| PGA | 114 | 46.0 ± 21.0 | 27.6 ± 15.6 | <0.0001 |
| CRP* | 114 | 1.37 ± 2.25 | 1.10 ± 1.97 | 0.0144 |

*the subjects with CRP < 0.3 were treated as CRP = 0.3

It was also observed that the changes in folate derivative absolute and relative concentrations, as well as MCP-1 concentrations following MTX therapy appear to be associated with the MTHFR 677C>T polymorphism.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of measuring the level of folate in a biological sample derived from a subject comprising measuring the level of any combination of various forms of folate selected from the group consisting of 5-methyltetrahydrofolate (5-MTHF), tetrahydrofolate (THF), and 5,10-MTHF or measuring the level of at least one of THF and 5,10-MTHF in said biological sample, wherein said measured level of any combination of various forms of folate selected from the group consisting of 5-MTHF, THF, and 5,10-MTHF or at least one of THF and 5,10-MTHF, is a measurement of said folate level in said biological sample.

2. The method of claim 1, wherein any combination of various forms of folate selected from the group consisting of 5-MTHF, THF, and 5,10-MTHF or at least one of THF and 5,10-MTHF is measured using a methodology selected from the group consisting of an isotope dilution liquid chromatography-multiple reaction monitoring/mass spectrometry (LC-MRM/MS), an antibody-based assay, a radiometric assay, a chromatographic assay, and a microbiological assay.

3. The method of claim 1, wherein the levels of any combination of various forms of folate selected from the group consisting of 5-MTHF, THF, and 5,10-MTHF or the levels of at least one of THF and 5,10-MTHF is a prediction of the level of total homocysteine (tHcy) in said biological sample.

4. The method of claim 3, wherein measuring any combination of various forms of folate selected from the group consisting of 5-MTHF, THF, and 5,10-MTHF or measuring at least one of THF and 5,10-MTHF as a prediction of the level of tHcy, results in a decreased incidence of misclassification of a subject as being hyperhomocysteineic compared with a method of predicting the level of tHcy that does not take into account levels of 5-MTHF, THF, and 5,10-MTHF.

5. The method of claim 3, wherein the level of THF and 5,10-methenylTHF is directly related to the level of tHcy.

6. The method of claim 3, wherein the levels of each 5-MTHF, THF, and 5,10-MTHF are expressed as a ratio value relative to each other such that the ratio value is predictive of a disease state or disease risk of said subject.

7. The method of claim 1, wherein when the levels of 5-MTHF, THF, and 5,10-MTHF are measured and are summed together, said summed level predicts the level of tHcy in said biological sample.

8. The method of claim 1, wherein said sample is selected from the group consisting of blood, serum, plasma, whole blood, plasma, serum, red blood cells, white blood cells, neutrophils, biopsy, spinal fluid, and cellular extracts.

9. A method of identifying a subject that is at risk of having a disease or condition associated with folate/homocysteine metabolism, said method comprising measuring the level of folate in a biological sample derived from said subject comprising measuring the level of any combination of various forms of folate selected from the group consisting of 5-MTHF, THF, and 5,10-MTHF or the level of at least one of THF and 5,10-MTHF in said biological sample, wherein said measured level of any combination of various forms of folate selected from the group consisting of 5-MTHF, THF, and 5,10-MTHF or the level of at least one of THF and 5,10-MTHF, is a measurement of said folate level in said biological sample, wherein a low level of folate in said biological sample compared to the folate level in a biological sample from an otherwise identical healthy subject identifies a subject at risk of having said disease or condition.

10. A method of evaluating the effect of an agent on a subject having a disease associated with folate/homocysteine metabolism, said method comprising comparing the level of any combination of various forms of folate selected from the group consisting of 5-MTHF, THF, and 5,10-MTHF or the levels of at least one of THF and 5,10-MTHF in a biological sample of a subject following administration of said agent to said subject, to the level of any combination of various forms of folate selected from the group consisting of 5-MTHF, THF, and 5,10-MTHF or the levels of at least one of THF and 5,10-MTHF in an otherwise identical biological sample of a subject not administered said agent, wherein an increased level of any combination of various forms of folate selected from the group consisting of 5-MTHF, THF, and 5,10-MTHF or an increased level of at least one of THF and 5,10-MTHF detected in said biological sample of said subject administered said agent compared to the level of any combination of various forms of folate selected from the group consisting of 5-MTHF, THF, and 5,10-MTHF or the level of at least one of THF and 5,10-MTHF in said otherwise identical biological sample is an indication that said agent increases folate levels in said subject, further wherein a decrease level of any combination of various forms of folate selected from the group consisting of 5-MTHF, THF, and 5,10-MTHF or a decrease level of at least one of THF and 5,10-MTHF detected in said biological sample of said subject administered with said agent compared to the level of any combination of various forms of folate selected from the group consisting of 5-MTHF, THF, and 5,10-MTHF or the level of at least one of THF and 5,10-MTHF in said otherwise identical biological sample of said subject not administered with said agent is an indication that said agent is able to decrease folate levels in said subject.

11. The method of claim 10, wherein said agent generates a side effect in said subject.

12. The method of claim 10, wherein said agent is selected from the group consisting of an anti-inflammatory agent, an anti-tumor agent, an anti-folate agent, a nutritional supplement, a dietary supplement, and a vitamin supplement, dietary regulator, and a chemical associated with smoking.

13. The method of claim 11, wherein said effect is selected from the group consisting of inflammation, oxidative stress, nausea, gastrointestinal disturbance, fatigue, and malaise.

14. A method of diagnosing a disease or condition associated with folate/homocysteine metabolism in a subject, said method comprising measuring the level of folate in a biological sample derived from a subject comprising measuring the level of any combination of various forms of folate selected from the group consisting of 5-MTHF, THF, and 5,10-MTHF or the level of at least one of THF and 5,10-MTHF in said biological sample, wherein said measured level of any combination of various forms of folate selected from the group consisting of 5-MTHF, THF, and 5,10-MTHF or the level of at least one of THF and 5,10-MTHF, is a measurement of said folate in said biological sample, wherein a low level of folate in said biological sample compared to the level of folate in a biological sample from an otherwise identical healthy subject identifies a subject at risk of having said disease or condition.

15. A method of monitoring the progression of a disease or condition associated with folate/homocysteine metabolism in a subject, said method comprising measuring the level of folate in a biological sample derived from said subject comprising measuring the level of any combination of various forms of folate selected from the group consisting of 5-MTHF, THF, and 5,10-MTHF or the level of at least one of THF and 5,10-MTHF in said biological sample, wherein said measured level of any combination of various forms of folate selected from the group consisting of 5-MTHF, THF, and 5,10-MTHF or the level of at least one of THF and 5,10-MTHF, is a measurement of said folate in said biological sample, wherein a low level of folate in said biological sample compared to the level of folate in a biological sample from said subject at an earlier time identifies progression of said disease or condition.

16. A method of monitoring the progression of a side effect in a subject, said method comprising measuring the level of folate in a biological sample derived from said subject comprising measuring the level of any combination of various forms of folate selected from the group consisting of 5-MTHF, THF, and 5,10-MTHF or the level of at least one of THF and 5,10-MTHF in said biological sample, wherein said measured level of any combination of various forms of folate selected from the group consisting of 5-MTHF, THE, and 5,10-MTHF or the level of at least one of THF and 5,10-MTHF, is a measurement of said folate in said biological sample, wherein a low level of folate in said biological sample compared to the folate level in a biological sample from said subject at an earlier time identifies progression of said side effect.

* * * * *